(12) United States Patent
Gillies et al.

(10) Patent No.: US 8,906,056 B2
(45) Date of Patent: Dec. 9, 2014

(54) ACCESS TROCAR AND RELATED METHOD THEREOF

(75) Inventors: George T. Gillies, Charlottesville, VA (US); Peter Pollak, Charlottesville, VA (US); Srijoy Mahapatra, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 6 days.

(21) Appl. No.: 13/318,450

(22) PCT Filed: Apr. 30, 2010

(86) PCT No.: PCT/US2010/033189
§ 371 (c)(1),
(2), (4) Date: Jan. 25, 2012

(87) PCT Pub. No.: WO2010/127259
PCT Pub. Date: Nov. 4, 2010

(65) Prior Publication Data
US 2012/0123461 A1    May 17, 2012

Related U.S. Application Data

(60) Provisional application No. 61/174,763, filed on May 1, 2009.

(51) Int. Cl.
*A61B 17/34* (2006.01)
*A61B 18/00* (2006.01)
*A61B 17/00* (2006.01)

(52) U.S. Cl.
CPC ..... *A61B 17/3423* (2013.01); *A61B 2017/3425* (2013.01); *A61B 2018/00392* (2013.01); *A61B 2017/00247* (2013.01); *A61B 2017/3413* (2013.01)
USPC .......................................... 606/185; 600/485

(58) Field of Classification Search
USPC ............ 606/184, 185; 600/485; 604/272, 506
See application file for complete search history.

(56) References Cited

U.S. PATENT DOCUMENTS 4,240,433 A    12/1980  Bordow
4,587,975 A *   5/1986  Salo et al. ..................... 600/506
(Continued)

FOREIGN PATENT DOCUMENTS

WO    WO 00/07652    2/2000
WO    WO 00/23000    4/2000
(Continued)

OTHER PUBLICATIONS

U.S. Appl. No. 61/174,763, filed May 1, 2009.
(Continued)

*Primary Examiner* — Victor Nguyen
(74) *Attorney, Agent, or Firm* — Robert J. Decker; Kilpatrick Townsend & Stockton LLP

(57) ABSTRACT

System and method that is directed to medical treatments of organs having anatomical spaces, such as (but not limited to) the heart and the pericardial space. Specifically, an apparatus and method is provided for safely accessing anatomical spaces with surfaces to deliver medical devices or media into such spaces, or to remove fluids from such spaces. The methods and apparatus may include a first elongated member with a sharp tip used to penetrate the surface surrounding the anatomical space with a second elongated member with a helical tine used to engage the surface and lift the surface away from the underlying anatomical space. Once the first elongated member has incised the surface, it is removed, and the incision may be used as a point of entry for delivering media or medical devices into the anatomical space, or for carrying out further medical procedures.

37 Claims, 23 Drawing Sheets

(56) References Cited

U.S. PATENT DOCUMENTS

| | | | |
|---|---|---|---|
| 5,125,888 | A | 6/1992 | Howard et al. |
| 5,354,283 | A | 10/1994 | Bark et al. |
| 5,538,504 | A | 7/1996 | Linden et al. |
| 5,707,335 | A | 1/1998 | Howard et al. |
| 5,779,694 | A | 7/1998 | Howard et al. |
| 6,132,438 | A | 10/2000 | Fleischman et al. |
| 6,156,009 | A | 12/2000 | Grabek |
| 6,162,195 | A | 12/2000 | Igo et al. |
| 6,216,030 | B1 | 4/2001 | Howard et al. |
| 6,272,370 | B1 | 8/2001 | Gillies et al. |
| 6,298,259 | B1 | 10/2001 | Kucharczyk et al. |
| 6,423,051 | B1 | 7/2002 | Kaplan et al. |
| 6,592,552 | B1 | 7/2003 | Schmidt |
| 6,599,274 | B1 | 7/2003 | Kucharczyk et al. |
| 6,626,902 | B1 | 9/2003 | Kucharczyk et al. |
| 6,890,295 | B2 * | 5/2005 | Michels et al. ............ 600/114 |
| 7,179,249 | B2 | 2/2007 | Steward et al. |
| 7,309,328 | B2 | 12/2007 | Kaplan et al. |
| 2002/0002363 | A1 | 1/2002 | Urakawa et al. |
| 2002/0103430 | A1 | 8/2002 | Hastings et al. |
| 2003/0195412 | A1 | 10/2003 | Gillies et al. |
| 2003/0204171 | A1 | 10/2003 | Kucharczyk et al. |
| 2005/0119556 | A1 | 6/2005 | Gillies et al. |
| 2005/0245896 | A1 | 11/2005 | Kucharczyk et al. |
| 2006/0025752 | A1 | 2/2006 | Broaddus et al. |
| 2008/0108945 | A1 | 5/2008 | Kaplan et al. |
| 2008/0262467 | A1 | 10/2008 | Humphrey et al. |
| 2009/0048577 | A1 | 2/2009 | Gillies et al. |
| 2009/0192487 | A1 | 7/2009 | Broaddus et al. |
| 2010/0042158 | A1 | 2/2010 | Broaddus et al. |
| 2010/0094143 | A1 | 4/2010 | Mahapatra et al. |
| 2010/0114093 | A1 | 5/2010 | Mahapatra et al. |
| 2010/0160896 | A1 | 6/2010 | Humphrey et al. |
| 2010/0198137 | A1 | 8/2010 | Broaddus et al. |
| 2010/0210927 | A1 | 8/2010 | Gillies et al. |
| 2010/0211064 | A1 | 8/2010 | Mahapatra et al. |

FOREIGN PATENT DOCUMENTS

| | | |
|---|---|---|
| WO | WO 2006/015091 | 2/2006 |
| WO | WO 2006/089243 | 8/2006 |
| WO | WO 2006/113267 | 10/2006 |
| WO | WO 2007/081842 | 7/2007 |
| WO | WO 2008/002595 | 1/2008 |
| WO | WO 2008/013709 | 1/2008 |
| WO | WO 2008/057370 | 5/2008 |
| WO | WO 2008/112870 | 9/2008 |
| WO | WO 2008/115745 | 9/2008 |
| WO | WO 2008/118737 | 10/2008 |
| WO | WO 2009/062061 | 5/2009 |

OTHER PUBLICATIONS

U.S. Appl. No. 07/904,032, filed Jun. 25, 1992.

Search Report corresponding to the PCT/US2010/033189 application.

* cited by examiner

ACCESS TROCAR AND RELATED METHOD THEREOF

RELATED APPLICATIONS

This application is a national stage application of International Application No. PCT/US2010/033189 filed Apr. 30, 2010 and claims priority under 35 U.S.C. §119(e) to U.S. Provisional Application Ser. No. 61/174,763, filed May 1, 2009, the disclosures of which are incorporated by reference herein in their entireties.

FIELD OF THE INVENTION

The present invention generally relates to medical treatments of organs having anatomical spaces, such as (but not limited to) the heart and the pericardial space. Specifically, the present invention relates to an apparatus and method for safely accessing anatomical spaces with surfaces to deliver medical devices or media into such spaces, or to remove fluids from such spaces.

BACKGROUND OF THE INVENTION

The heart muscle is surrounded by tissue known as the pericardial sac, which consists of several layers of tissue. The outermost of these layers is the fibrous pericardium. Inside the fibrous pericardium is the serous pericardium. The serous pericardium consists of three parts: the parietal pericardium, which is bonded to the inside of the fibrous pericardium; the innermost visceral pericardium; and a fluid-containing potential space between the parietal pericardium and the visceral pericardium called the pericardial space. Inside the visceral pericardium is the myocardium, the actual heart muscle itself.

Epicardial procedures on the heart are growing in number, efficacy, and complexity. Currently, ablations for ventricular tachycardia and atrial fibrillation as well as intra-cardiac procedures for valve repair are done using approaches on the outside of the heart. Establishing epicardial access is often difficult and frequently requires the assistance of a surgeon. Similar difficulties exist in establishing access to other anatomical spaces with surfaces, such as the kidneys, the dura mater of the brain, blood vessels, and the peritoneum.

Several conventional devices establish access to such anatomical spaces using vacuum or forceps. One problem with vacuum designs is that it is difficult to maintain the vacuum seal on the pericardium required to create and uphold a bleb. Additionally, if the vacuum seal is broken, the tissue bleb may re-collapse away from the tip of the suction probe, thus interrupting the procedure. Vacuum suction is also likely to cause trauma and scarring to the pericardium. Moreover, vacuum designs are likely to clog on other bodily tissues encountered before reaching the pericardium. Forceps designs also pose several problems. First, forceps designs provide an uncertain grasp on the pericardium. Second, forceps devices require such shallow approach angles that they often have difficulty grasping the pericardium. Moreover, such forceps devices require that large incisions be made in the subject in order to provide a large enough window to facilitate their use.

Conventional approach with penetration devices and access tubes do not grip the anatomical surface with uniform force, increasing the risk of tearing. Additionally, significant mechanical difficulties are encountered with fat and other tissue in the body before reaching the anatomical surface, as fat and tissue may become caught in the penetrating elements and restrict further movement.

There is therefore a need in the art for a safe, consistent, accurate, and easy to use percutaneous system to access the pericardial space. Similar needs arise in the context of accessing other anatomical spaces with surfaces as well.

SUMMARY OF THE INVENTION

By practicing the methods and apparatus of various embodiments of the present invention, the skilled practitioner can easily and safely access the underlying anatomical space. An aspect of an embodiment of the present invention provides, but not limited thereto, a first elongated member with a sharp tip used to penetrate the surface surrounding the anatomical space with a second elongated member with a helical tine used to engage the surface and lift the surface away from the underlying anatomical space. Once the first elongated member has incised the surface, it is removed, and the incision may be used as a point of entry for delivering media or medical devices into the anatomical space, or for carrying out further medical procedures.

An aspect of an embodiment of the present invention may be used to access any anatomical space with a surface. Anatomical spaces that may be accessed with various embodiments may include but are not limited to the pericardial space, the interior of the kidneys, the brain, blood vessels, the peritoneal cavity, the spinal cord, the intra-abdominal space, the intra-thoracic space or any space in the body bounded by a membrane or membranous entity. Surfaces include but are not limited to the parietal pericardium, the renal capsule, the dura mater, blood vessel walls, the peritoneum, the dural lining of the spinal cord, the pleura, the seurosa, or any other membrane in the body. It should be appreciated that the various embodiments may be practiced not only upon human subjects but upon animal subjects as well.

Media may comprise a pharmaceutically active substance, cells, fluids, biological fluids, drugs, gene therapy vectors, irrigation fluids, growth factors, nuclear medicine agents, antibiotics, anti-viral agents, contrast agents, chemotherapies, or other diagnostic or therapeutic agents.

Medical devices may include but are not limited to sheath catheters, ablation catheters, guide wires, other catheters, visualization and recording devices, lumens, steering devices or systems, drug or cell delivery catheters, fiber endoscopes, suctioning devices, irrigation devices, electrode catheters, needles, optical fiber sensors, sources of illumination, vital signs sensors, pacing leads, cathode or other electrodes, fluid delivery or removal means, devices for delivering and unfurling or spreading surface patches or coverings onto the heart, biopsy devices, suture- or staple-placement devices, endoscopes, fiber-optic probes, temperature sensors, pH or other chemical sensors, feedback or regulation devices, batteries or other energy sources, cryoprobes, laser light delivery probes, artherectomy devices, angioplasty devices, surgical devices, and the like.

An advantage conferred by an aspect of an embodiment of the present invention is that the single point of contact made helical tine minimizes the resistance faced by the apparatus as it passes through other tissue such as fat and muscle in order to reach the surface of the anatomical space. Another advantage of using aspect of an embodiment of the present invention is a minimized risk of tearing the anatomical surface as it is lifted away from the anatomical space, since the helical tine provides a stable and uniform distribution of lift across the anatomical surface after it has engaged the surface. Thus, the teachings of the present invention overcome the limitations of the prior art devices by consistently, safely, and stably lifting the surface from the anatomical space in order to establish access to the anatomical space.

An aspect of an embodiment of the present invention provides methods and apparatus used to implement a novel approach for accessing anatomical spaces with surfaces safely, consistently, accurately, and with ease. An aspect of an embodiment of present the invention, the apparatus is advanced through the body to abut the parietal pericardium or other anatomical surface. The apparatus is then turned so that the helical tine of the second elongated member penetrates and engages the surface and draws it in a proximal direction, thereby enlarging the anatomical space and pulling the surface onto the sharpened first elongated member, causing the first elongated member to incise the anatomical surface. Once the anatomical surface has been penetrated, the first elongated member is withdrawn in a proximal direction. After the first elongated member has been at least partially withdrawn, medical devices or media may be inserted through the incision into the anatomical space, with the second elongated member left in place in order to maintain the expansion of the anatomical space. In an aspect of an embodiment of this method, the medical devices or media are inserted into the anatomical space through the second elongated member while its helical tine remains engaged with the surface.

In an aspect of an embodiment of the present invention, the apparatus is advanced through the body to abut the parietal pericardium or other anatomical surface. The apparatus is then turned so that the helical tine of the second elongated member penetrates and engages the surface and draws it in a proximal direction, thereby enlarging the anatomical space and pulling the surface onto the sharpened first elongated member, causing the first elongated member to incise the anatomical surface. Once the anatomical surface has been penetrated, the first elongated member is withdrawn in a proximal direction. After the first elongated member has been withdrawn, a guide wire may be inserted through the incision into the anatomical space. Once the guide wire has been inserted into the anatomical space, the second elongated member is rotated so that its helical tine disengages from the surface. Once the second elongated member is no longer engaged with the surface, it is withdrawn in a proximal direction.

In an aspect of an embodiment of the present invention, the apparatus may be equipped with actuating means to control precisely the movement of the helical tine in order to improve the safety of access procedures and to stabilize the helical tine's grip on the surface.

An aspect of an embodiment of the present invention may comprise imaging components of the apparatus so that the practitioner may determine the position of the device within the subject's body. For example, the sharp end of the first elongated member may be adapted to be used with an imaging device. In a currently preferred embodiment, the sharp end is echogenic, meaning that it is adapted to scatter ultrasonic waves. By using an ultrasonic transducer in conjunction with an imaging device and in conjunction with the echogenic sharp end, the practitioner of the invention may precisely determine the position of the sharp end of the first elongated member within the body. In an embodiments, any component of any embodiment of the apparatus may be adapted for use with ultrasound or with other medical imaging modalities, including but not limited to magnetic resonance imaging, computed tomography, fluoroscopy, or other radiological modalities.

An aspect of an embodiment of the present invention provides an apparatus for accessing a subject's anatomical space having a surface. The apparatus may comprise: a first elongated member comprising a proximal end and a distal end, wherein the distal end includes a sharp end or portion. The apparatus may comprise: a second elongated member comprising a proximal end and a distal end, wherein the distal end includes a helical tine. The helical tine is configured to: engage and penetrate the surface of the anatomical space, wherein when the second elongated member is turned the helical tine lifts the surface in a proximal direction. This lifting assists in advancing the surface in contact with the sharp end (or portion) to cause an incision of the surface by the sharp end (or portion).

An aspect of an embodiment of the present invention provides a method for accessing a subject's anatomical space having a surface. The method may comprise: providing a first elongated member having a proximal end and a distal end, wherein the distal end includes a sharp end or portion. The method may further comprise: providing a second elongated member having a proximal end and a distal end, wherein the distal end includes a helical tine. The method may further comprise: engaging the surface of the anatomical space with the helical tine. The method may further comprise: turning the helical tine to cause lifting of the surface in a proximal direction, whereby the lifting assists in advancing the surface in contact with the sharp end or portion to cause an incision of the surface by the sharp end or portion.

System and method that is directed to medical treatments of organs having anatomical spaces, such as (but not limited to) the heart and the pericardial space. Specifically, an apparatus and method is provided for safely accessing anatomical spaces with surfaces to deliver medical devices or media into such spaces, or to remove fluids from such spaces. The methods and apparatus may include a first elongated member with a sharp tip used to penetrate the surface surrounding the anatomical space with a second elongated member with a helical tine used to engage the surface and lift the surface away from the underlying anatomical space. Once the first elongated member has incised the surface, it is removed, and the incision may be used as a point of entry for delivering media or medical devices into the anatomical space, or for carrying out further medical procedures.

An aspect of an embodiment of the present invention may comprise sensing the pressure regimes of the subject's body so that the practitioner may accurately navigate the device within the subject's body. An embodiment of this aspect may comprise an access needle configured to monitor pressures as the access needle is advanced through the body.

The invention itself, together with further objects and attendant advantages, will best be understood by reference to the following detailed description taken in conjunction with the accompanying drawings.

BRIEF DESCRIPTION OF THE DRAWINGS

The accompanying drawings illustrate several aspects and embodiments of the present invention, and, together with the description herein, serve to explain the principles of the invention. The drawings are provided only for the purpose of illustrating select embodiments of the invention and are not to be construed as limiting the invention.

DESCRIPTION OF THE SPECIFIC EMBODIMENTS

Figure 1:
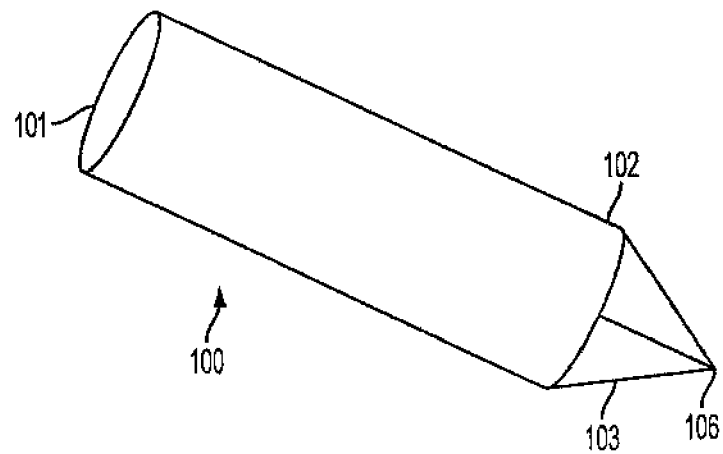
FIG. 1 depicts an embodiment of the first elongated member

FIG. 1 shows an embodiment of the first elongated member 100. This elongated member comprises a proximal end 101 and a distal end 102. Disposed at the distal end 102 is a sharp end 103 that may be configured so as to provide a sharp point 106. It should be appreciated that the sharp end may be a variety of sharp structures or points such as beveled structure, serrated structure, tapered structure, or cutting edge structure, etc. In an approach, the first elongated member 100 may be configured as a cylinder, rectangular, prism, tube, shaft or other geometric shape as desired or required, with a length of about 1 cm to about 40 cm or as desired or required, and a width of about 1 mm to about 15 mm or as desired or required. It should be appreciated that that other lengths, shapes, contours and cross-sections may be used. The first elongated member 100 may be hollow or solid. The sharp point 106 may be configured as any one of a variety of structures, including but not limited to beveled structure, serrated structure, tapered structure, or cutting edge structure. In an embodiment, the first elongated member 100 may be composed of surgical-grade stainless steel, such as 306 stainless steel. In other embodiments, the first elongated member 100 may be composed of materials selected to be compatible with various medical imaging modalities, including but not limited to ferrous metals and alloys; non-ferrous metals and alloys such as titanium, nitinol, or magnesium; or plastics.

Figure 2:
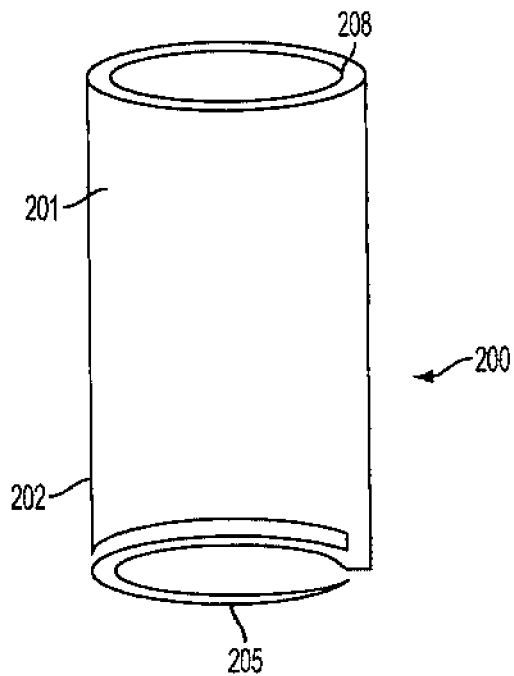
FIG. 2 depicts an embodiment of the second elongated member.

FIG. 2 shows an embodiment of the second elongated member 200 of the invention. This elongated member comprises a proximal end 201 and a distal end 202. Disposed at the distal end 202 is a helical tine 205 configured as a corkscrew or the like. The axis of the helical tine 205 may be angled with respect to the longitudinal axis defined by the second elongated member 200 at a range of varying degrees from 0 degrees to 90 degrees, and preferably between about 10 and about 35 degrees, or as desired or required, so that when turned it can engage the anatomical surface. The helical tine 205 may subtend about 30 degrees of arc to about 360 degrees of arc, or as desired or required. Running through the second elongated member 200 is at least one lumen 208. In an embodiment, the second elongated member 200 is configured as a cylinder, cylinder, rectangular, prism, tube, hollow shaft or other geometric shape as desired or required, with a length of about 1 cm to about 40 cm or as desired or required and a width of about 1 mm to about 15 mm or as desired or required. It should be appreciated that other lengths, shapes, contours and cross-sections may be used. In an embodiment, the second elongated member 200 may be composed of surgical-grade stainless steel, such as 306 stainless steel. In other embodiments, the second elongated member 200 may be composed of materials selected to be compatible with various medical imaging modalities, including but not limited to ferrous metals and alloys; non-ferrous metals and alloys such as titanium, nitinol, or magnesium; or plastics. In an embodiment, the shape of the lumen 208 is also adapted to house the first elongated member 100.

Figure 3:
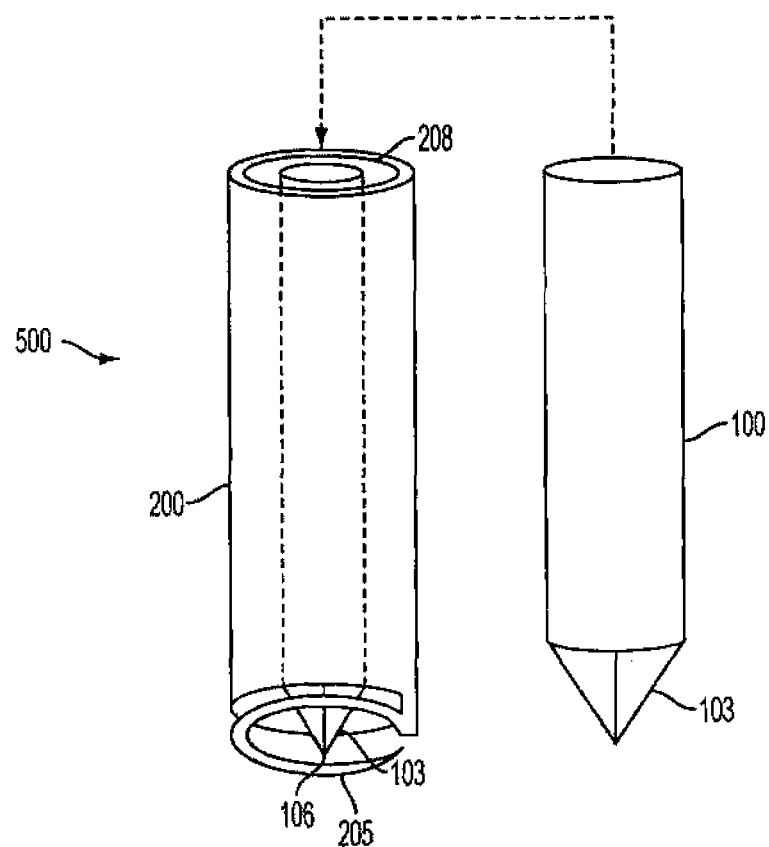
FIG. 3 depicts the embodiment of the first elongated member of FIG. 1 and the embodiment of the second elongated member of FIG. 2 used in tandem, with the first elongated member housed inside the second elongated member.
Figure 13:
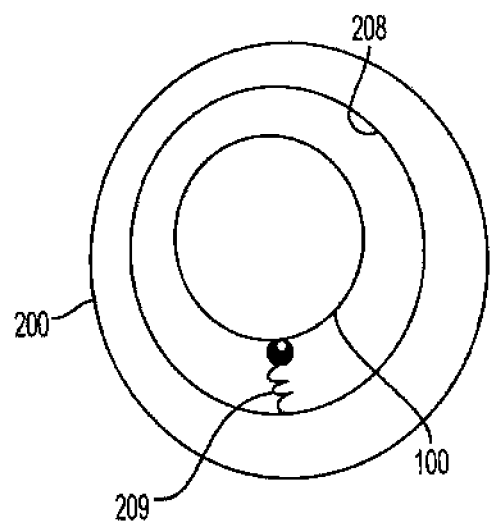
FIG. 13 is a top-down cross-section view of an embodiment of the means used to hold the first elongated member in a fixed position with respect to the second elongated member.

FIG. 3 shows an embodiment of the apparatus 500 comprising the first elongated member 100 and the second elongated member 200. The first elongated member is inserted through the lumen 208 of the second elongated member 200 and housed therein. In an embodiment, the two elongated members may be selectively held in a fixed position relative to each other. It should be appreciated that the means for the selective holding may be a variety of approaches. For example, FIG. 13 depicts an embodiment of this selective hold aspect comprising switchable spring-ball mechanism 209 comprising a non-deformable high friction ball attached to a spring disposed inside the lumen 208 of the second elongated member 200. The ball of the spring-ball mechanism 209 presses against the first elongated member 100 and holds it in place inside the lumen 208. Moreover, for example, grooves, high-friction materials, or other structures disposed on either the first elongated member 100 or the second elongated member 200 may also be employed to hold or selectively hold the two elongated members in a fixed position with respect to each other.

Figure 4:
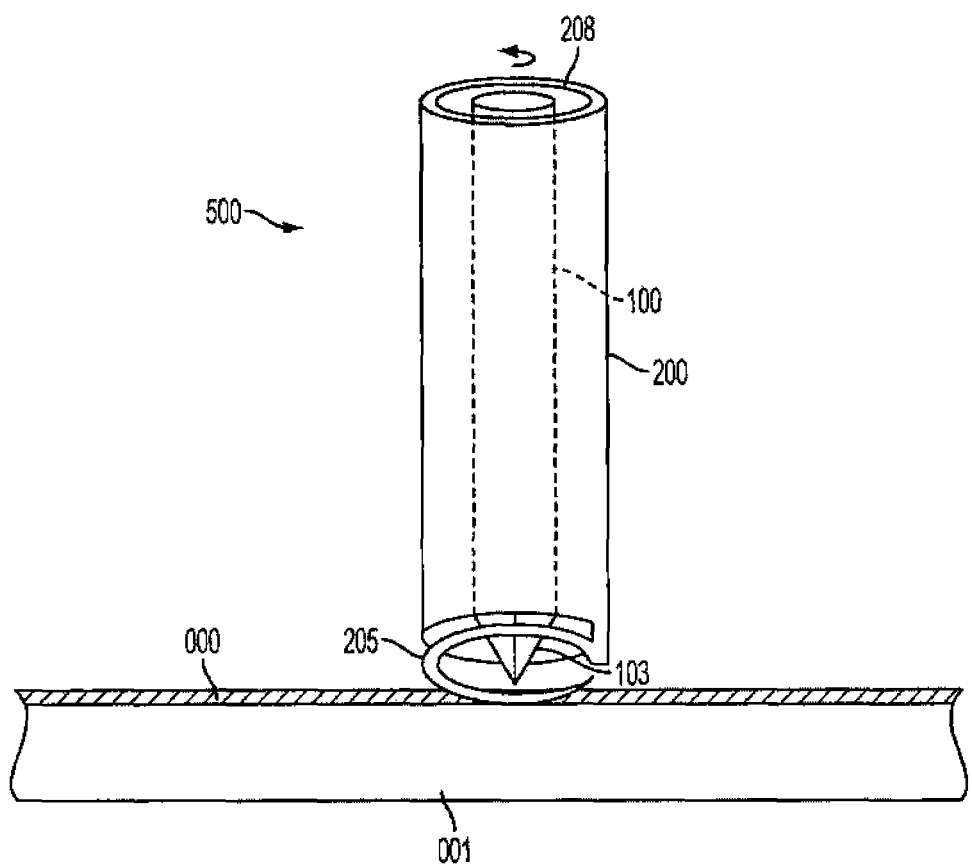
FIG. 4 depicts the embodiment in FIG. 3 in use as it engages the anatomical surface.
Figure 5:
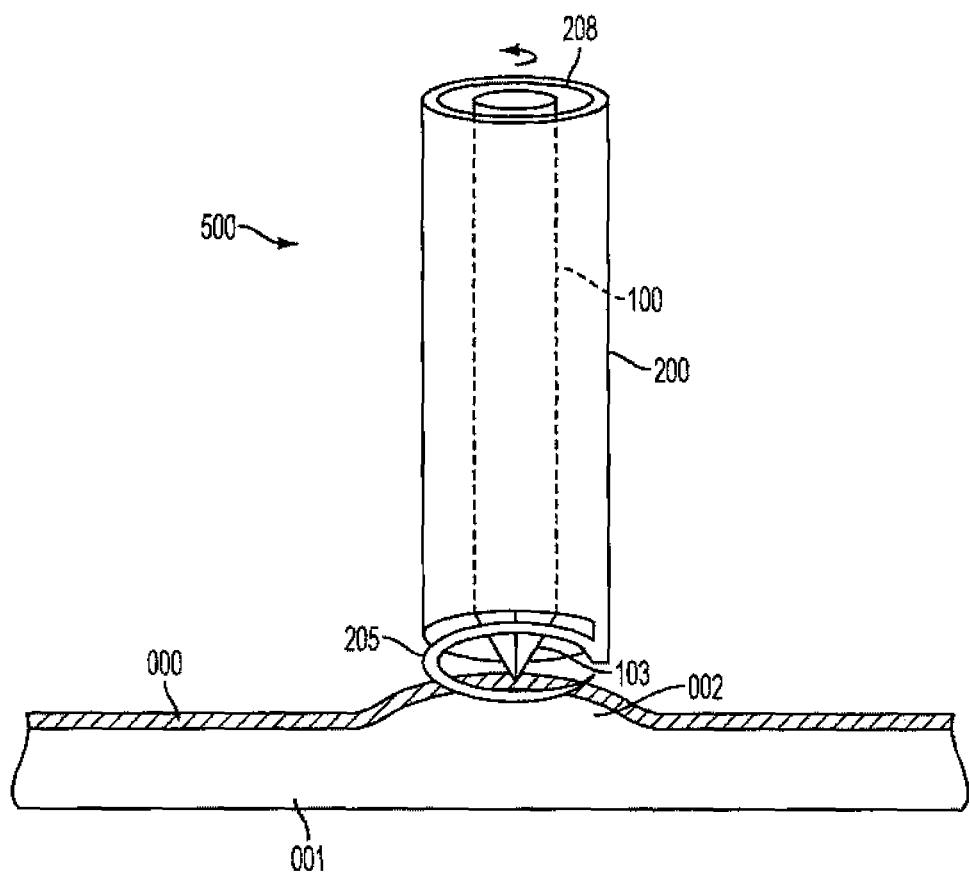
FIG. 5 depicts the embodiment in FIG. 3 in use as it enlarges the anatomical space.
Figure 6:
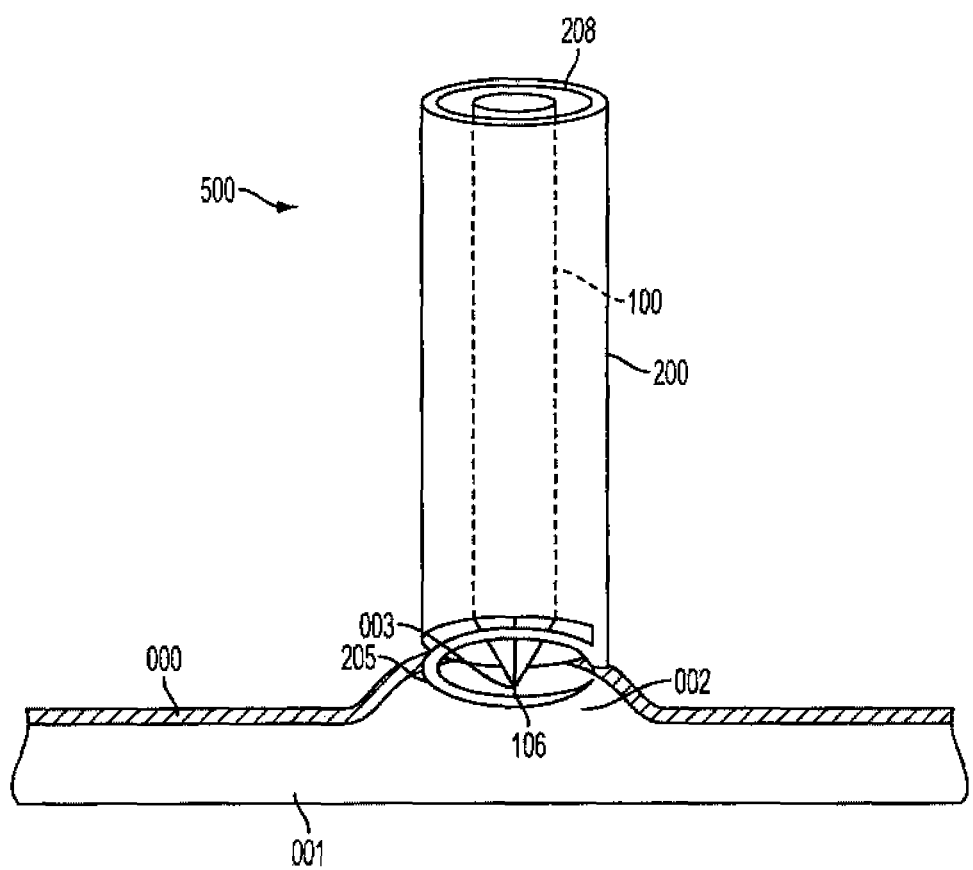
FIG. 6 depicts the embodiment in FIG. 3 in use as it penetrates the anatomical surface.

FIGS. 4-6 depict the embodiment of the apparatus 500 in use. Once the apparatus is in place or adjacent to the surface 000 of the anatomical space 001, as shown in FIG. 4, the helical tine 205 can engage and penetrate the surface 000 when it rotated. As shown in FIG. 5, as the helical tine is rotated, the helical tine 205 draws (or advances) the surface 000 in a proximal direction, causing an expansion of the anatomical space 002. As shown in FIG. 6, the helical tine may continue to be turned so as to cause the helical tine 205 to draw (or advance) the surface 000 onto the sharp point 106 (or sharp end 103) of the first elongated member 100 so as to cause an incision 003 in the surface 000 by the sharp point 106. It should be appreciated that in addition to the rotation of the helical tine 205, the incision 003 by the sharp point 106 may be also be effected by 1) moving the first elongated member 100 in a distal direction, 2) moving the second elongated member 200 in a proximal direction, or 3) moving the first elongated member 100 in a distal direction and moving the second elongated member 200 in a proximal direction. It should be appreciated that any of the drawing (advancing) and moving (distally/proximally) may be accomplished simultaneously, sequentially or any combination thereof.

Figure 7:
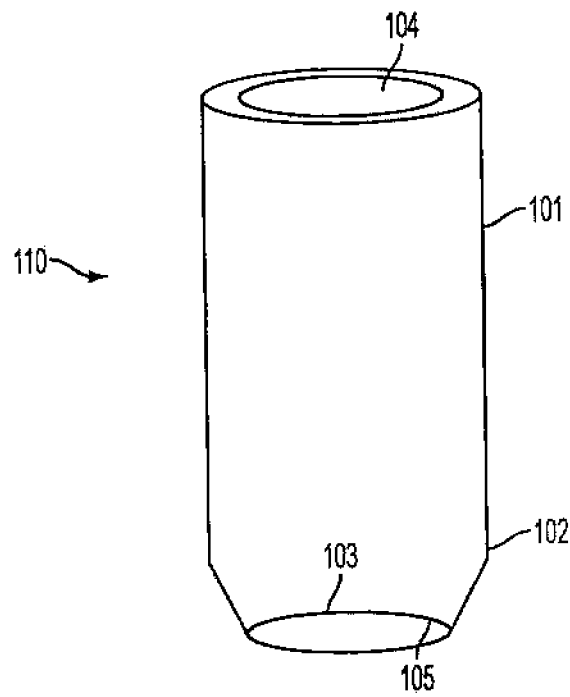
FIG. 7 depicts the first elongated member of an alternate embodiment.

FIG. 7 depicts an embodiment of the first elongated member 110. This elongated member comprises a proximal end 101 and a distal end 102. Disposed at the distal end 102 is a sharp end 103 configured as a sharp rim 105. Running through the alternate first elongated member 110 is a lumen 104. In an approach, the first elongated member 110 may be configured as a cylinder, rectangular, prism, tube, hollow shaft or other geometric shape as desired or required, with a length of about 1 cm to about 40 cm or as desired or required and a width of about 1 mm to about 15 mm or as desired or required. It should be appreciated that that other lengths, shapes, contours, and cross-sections may be used. In an embodiment, the first elongated member 110 is composed of surgical-grade stainless steel, such as 306 stainless steel. In other embodiments, the first elongated member 110 may be composed of materials selected to be compatible with various medical imaging modalities, including but not limited to ferrous metals and alloys; non-ferrous metals and alloys such as titanium, nitinol, or magnesium; or plastics. In an embodiment, the lumen 104 of the first elongated member 110 may be adapted to house the second elongated member 210, shown in FIG. 8. It should be appreciated that the lumen 104 and the second elongated member 210 may be configured to accommodate other devices or structures. In an embodiment, the second elongated member 210 may be hollow or solid.

Figure 8:
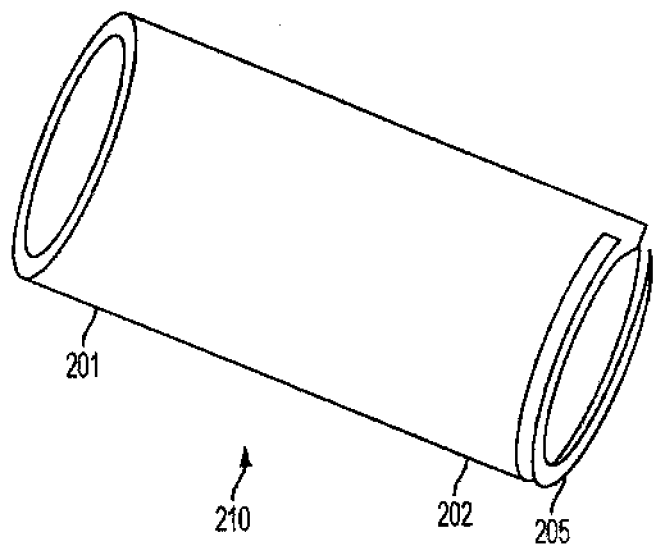
FIG. 8 depicts the second elongated member of an alternate embodiment.

FIG. 8 shows an embodiment of the second elongated member 210 of the invention. This elongated member comprises a proximal end 201 and a distal end 202. Disposed at the distal end 202 is a helical tine 205 configured as a corkscrew or the like. The axis of helical tine 205 may be angled with respect to the longitudinal axis defined of the second elongated member 200 at a range of varying degrees from about 0 degrees to about 90 degrees, and preferably between 10 and 35 degrees, or as desired or required, so that when turned it can engage the anatomical surface. The helical tine 205 may subtend about 30 degrees of arc to about 360 degrees of arc, or as desired or required. Running through the second elongated member 200 is at least one lumen 208. In an embodiment, the second elongated member 200 is configured as a cylinder, cylinder, rectangular, prism, tube, hollow shaft or other geometric shape as desired or required, with a length of about 1 cm to about 40 cm or as desired or required and a width of about 1 mm to about 15 mm or as desired or required. It should be appreciated that other lengths, shapes, contours, and cross-sections may be used. In an embodiment, the second elongated member 210 may be composed of surgical-grade stainless steel, such as 306 stainless steel. In other embodiments, the second elongated member 200 may be composed of materials selected to be compatible with various medical imaging modalities, including but not limited to ferrous metals and alloys; non-ferrous metals and alloys such as titanium, nitinol, or magnesium; or plastics.

Figure 9:
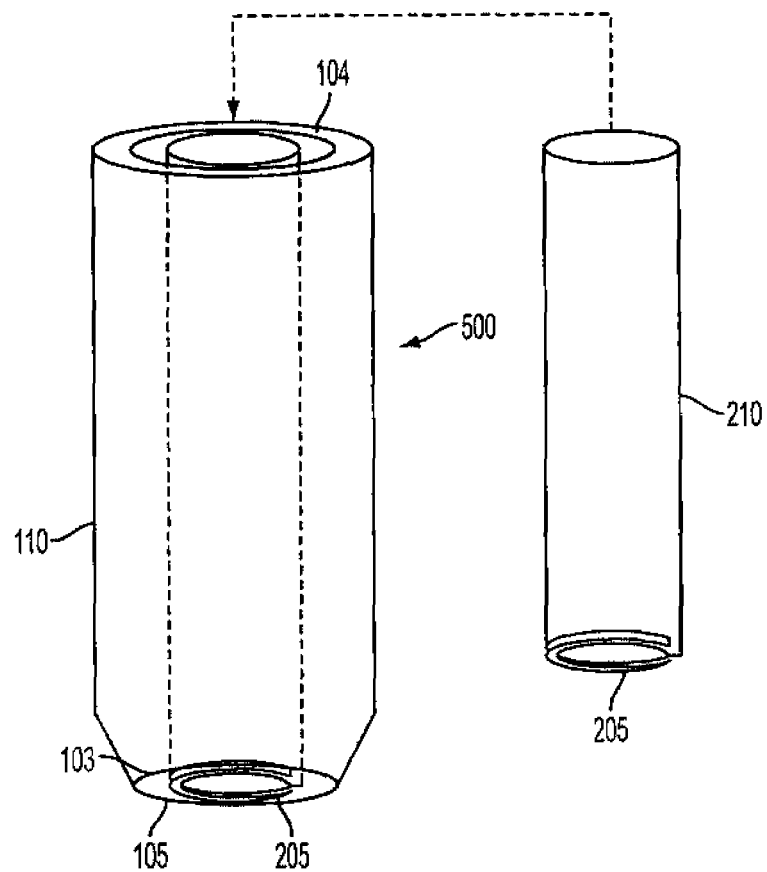
FIG. 9 depicts the embodiment of the first elongated member of FIG. 7 and the embodiment of the second elongated member of FIG. 8 used in tandem, with the second elongated member housed inside the first elongated member.

FIG. 9 shows an embodiment of the apparatus 500 comprising the first elongated member 110 and the second elongated member 210. The second elongated member 210 is inserted through the lumen 104 of the first elongated member 110 and housed therein. In a currently preferred embodiment, the two elongated members may be selectively held in a fixed position relative to each other.

Figure 10:
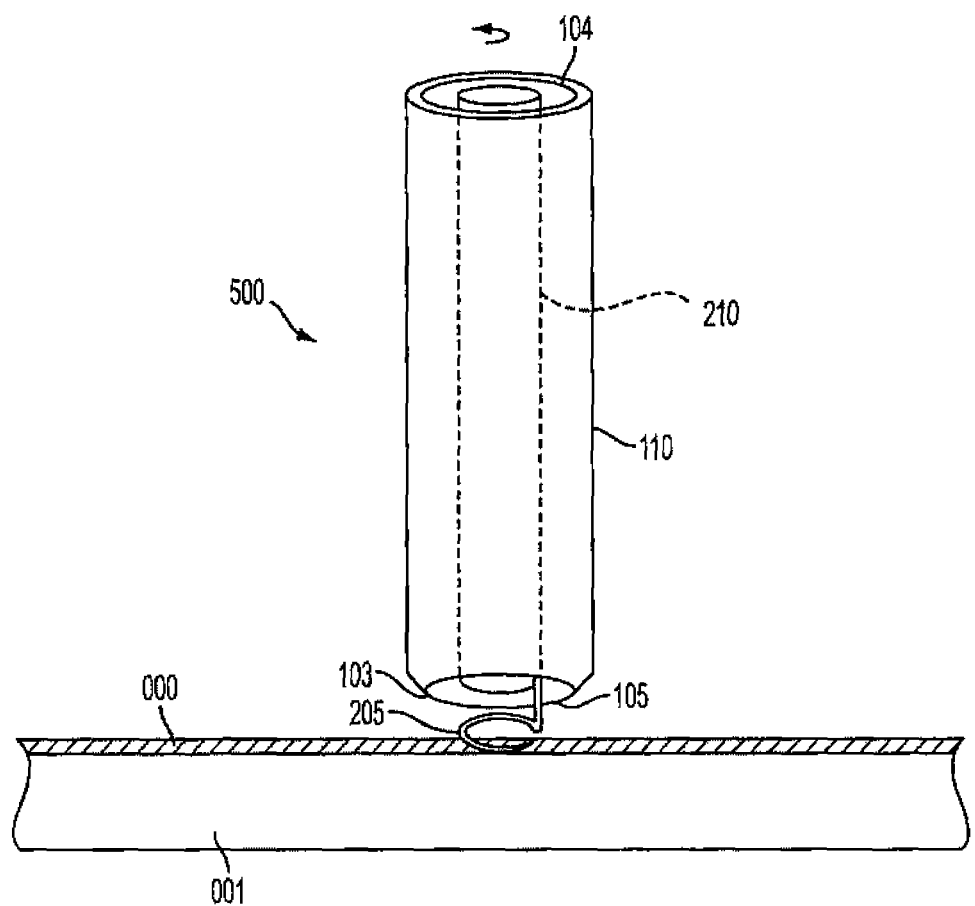
FIG. 10 depicts the embodiment in FIG. 9 in use as it engages the anatomical surface.
Figure 11:
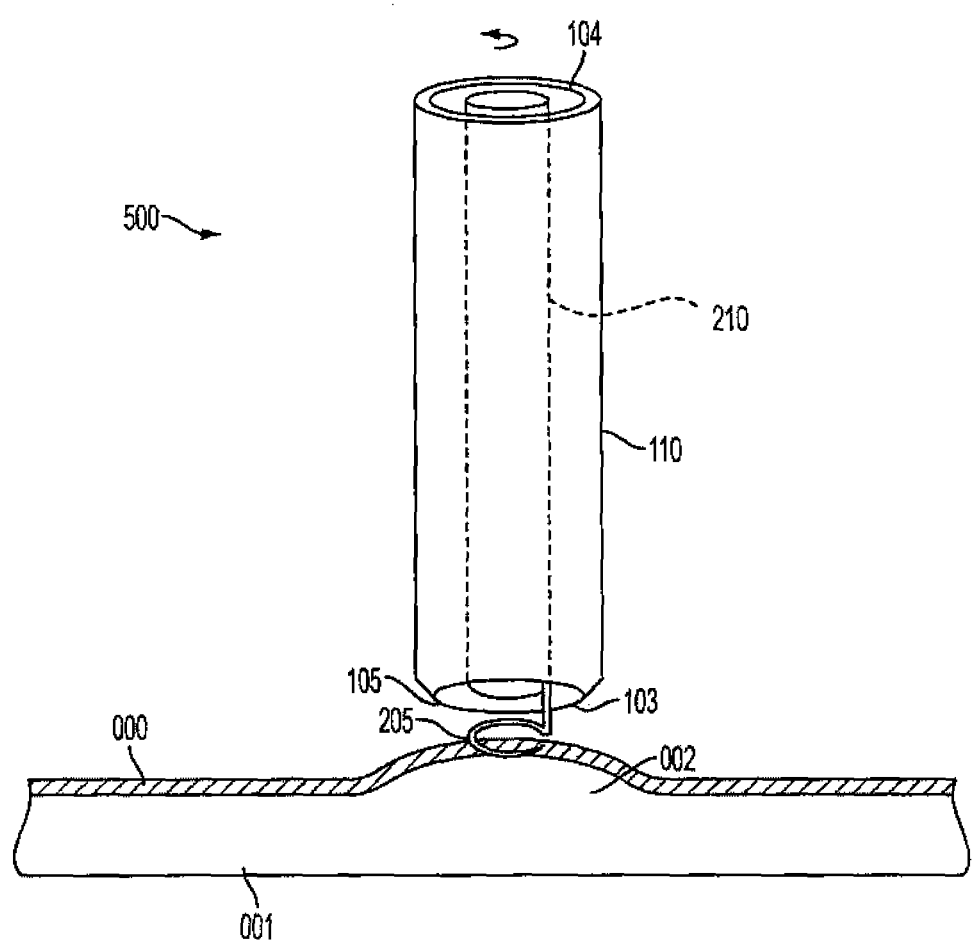
FIG. 11 depicts the embodiment in FIG. 9 in use as it enlarges the anatomical space.
Figure 12:
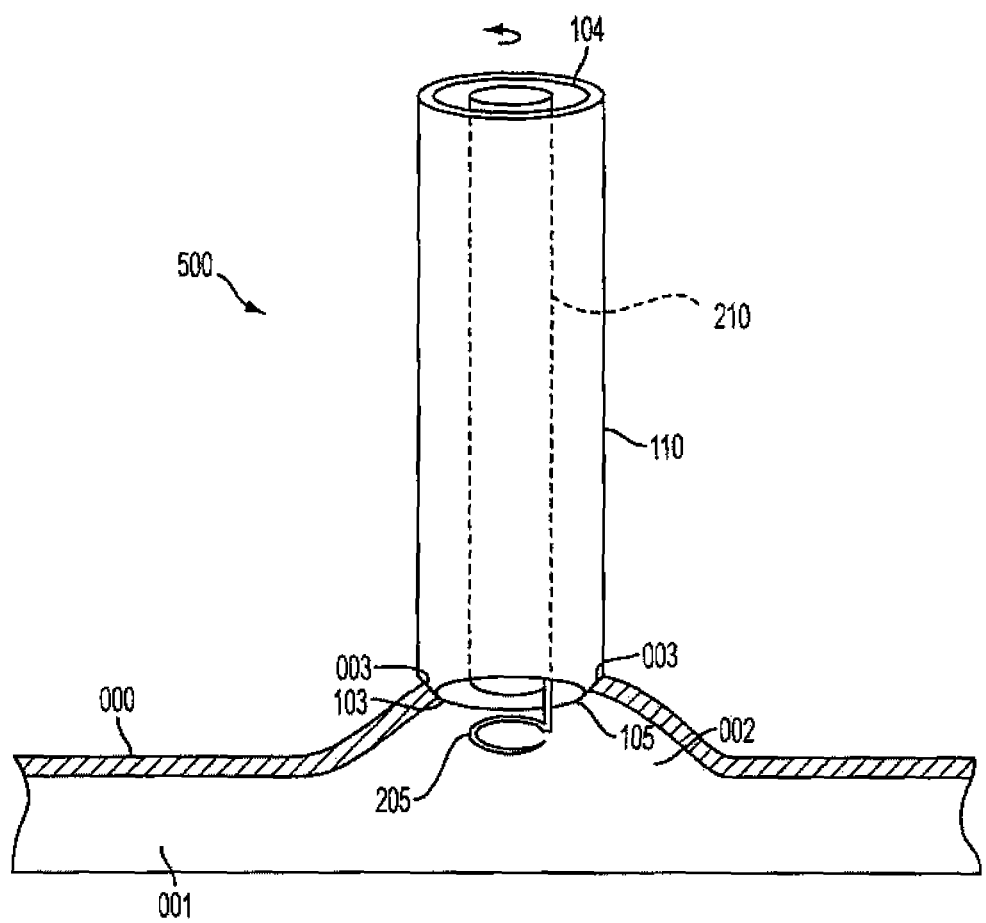
FIG. 12 depicts the embodiment in FIG. 9 use as it penetrates the anatomical surface.

FIGS. 10-12 depicts an embodiment of the apparatus 500 in use. Once the apparatus is in place or adjacent to the surface 000 of the anatomical space 001, as shown in FIG. 10, the helical tine 205 can engage and penetrate the surface 000 when it is rotated. As shown in FIG. 11, as the helical tine 205 is rotated, the helical tine 205 draws (or advances) the surface 000 in a proximal direction, causing an expansion of the anatomical space 002. As shown in FIG. 12, the helical tine 205 may continue to be turned so as to cause the helical tine 205 to draw (or advance) the surface 000 onto the sharp rim 105 of the first elongated member so as to cause incisions 003 in the surface 000 by the sharp rim 105. It should be appreciated that in addition to the rotation of the helical tine 205, the incision 003 by the sharp rim 105 may be also be effected by 1) moving the first elongated member 100 in a distal direction, 2) moving the second elongated member 200 in a proximal direction, or 3) moving the first elongated member 100 in a distal direction and moving the second elongated member 200 in a proximal direction. It should be appreciated that any of the drawing (advancing) and moving (distally/proximally) may be accomplished simultaneously, sequentially or any combination thereof.

Figure 14:
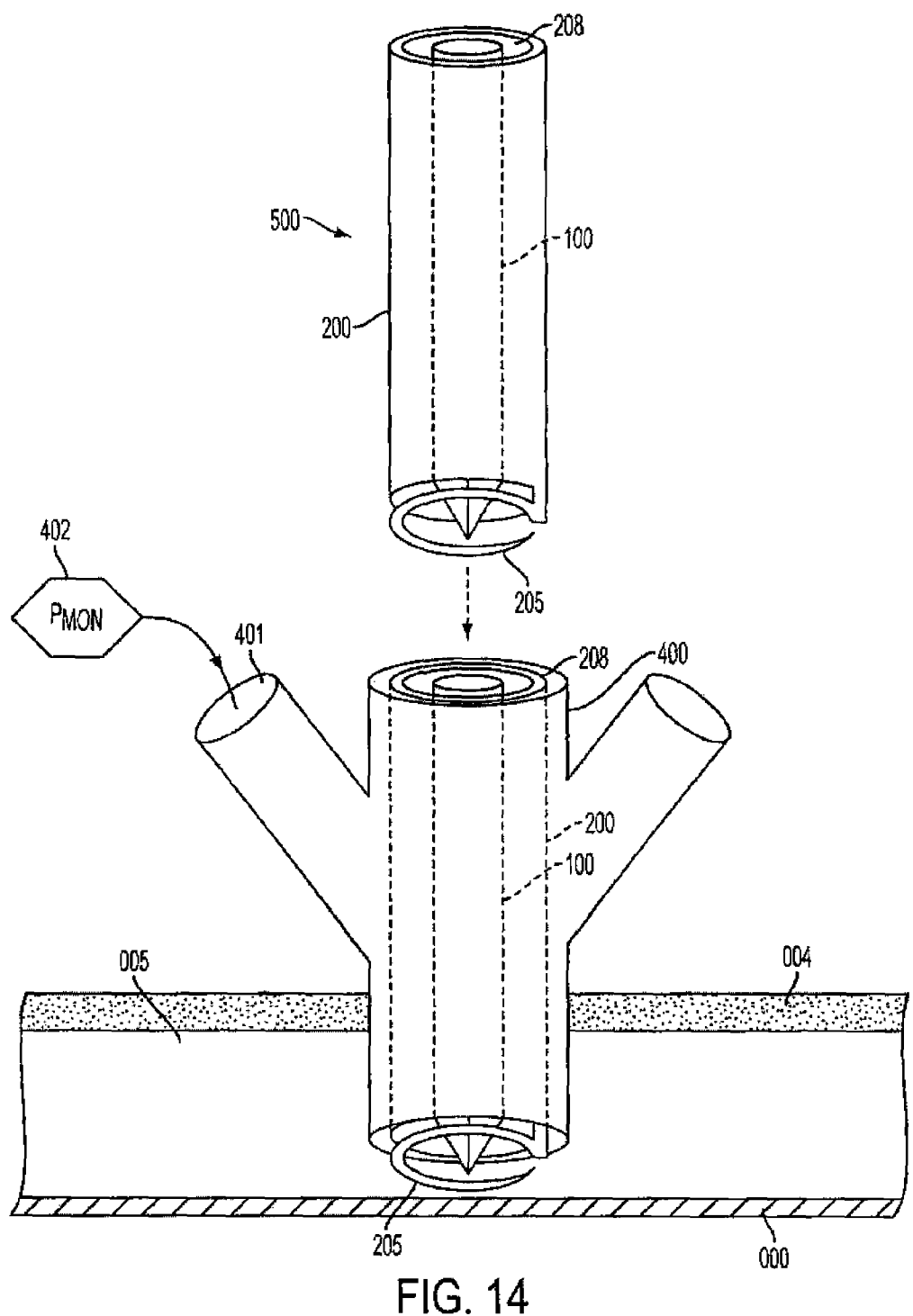
FIG. 14 depicts the embodiment of the invention in FIG. 3 used in conjunction with an access needle and pressure-sensing means.

FIG. 14 depicts an embodiment of the apparatus 500 used in conjunction with an embodiment of an access needle 400 (i.e., access device) disclosed in PCT International Application Serial No. PCT/US2008/056643, filed Mar. 12, 2008, (Pub. No. WO/2008/115745, published Sep. 25, 2008), entitled "Access Needle Pressure Sensor Device and Method of Use,", and its corresponding U.S. National Stage application Ser. No. 12/530,830, filed Sep. 11, 2009; of which the disclosure are hereby incorporated by reference herein in their entirety. In an embodiment, the access needle 400 is advanced through the subject's skin 004 and thorax 005 until it is near the surface 000 of the anatomical space to be accessed. The apparatus 500 is first presented (as shown in the top portion of the drawing sheet) then advanced through the access needle 400 (as shown in the lower portion of the drawing sheet). The access needle 400 may optionally further comprise a pressure monitoring system 402 in communication with a side port 401 of the access needle 400. The pressure monitoring system 402 may employ any number or type of pressure sensors, including sensors that are manometric, solid-state, optical, or otherwise sensitive to hydrostatic and hydrodynamic pressures. Moreover, other devices that the access device (access needle) may accommodate with the practice of this invention include, but not limited thereto, the following: ablation catheters, guidewires, pacing leads, pacing catheters, pacemakers, visualization and recording devices, drugs, and drug delivery devices, lumens, steering devices or systems, drug or cell delivery catheters, fiber endoscopes, suctioning devices, irrigation devices, electrode catheters, needles, optical fiber sensors, sources of illumination, vital signs sensors, and the like Theses devices may be deployed for procedures in an integral body part or space.

Figure 15:
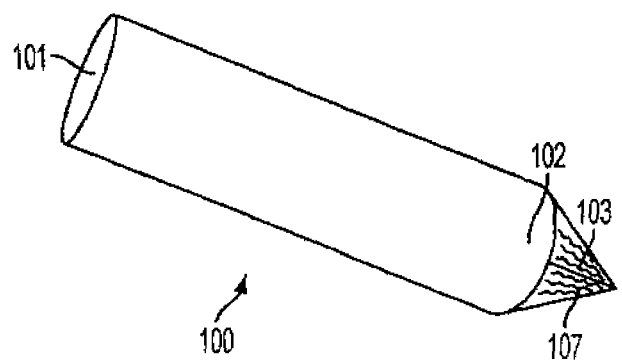
FIG. 15 depicts an embodiment of the first elongated member of FIG. 1 adapted for use with an imaging system.
Figure 16:
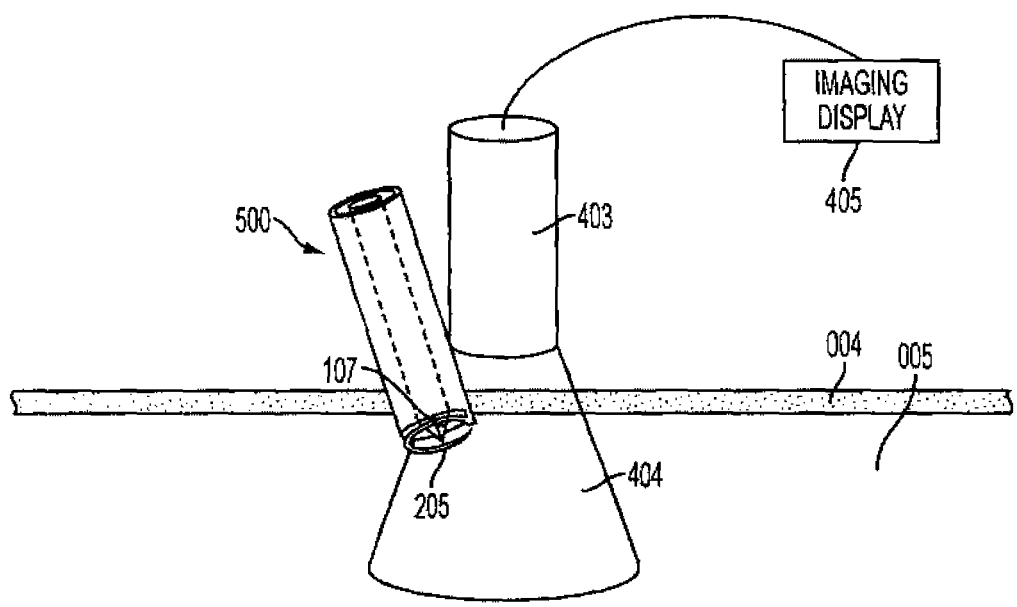
FIG. 16 depicts an embodiment of the invention incorporating an imaging system and the first elongated member depicted in FIG. 15.

FIGS. 15-16 depict an embodiment of the first elongated member 100 of the apparatus 500 adapted for use with a medical imaging modality. In an embodiment, the sharp end 103 of the first elongated member 100 comprises etchings 107 capable of scattering ultrasonic waves 404 generated by an ultrasonic transducer 403 connected to an imaging display 405 capable of displaying the combination apparatus' position under the skin 004. However, several modifications may be made upon this embodiment. Any part of any constituent of the apparatus 500 could be modified for use with the ultrasonic transducer 403 or for use with any other medical imaging modality, including but not limited to magnetic resonance imaging, computed tomography, fluoroscopy, or other radiological modalities.

Figure 17:
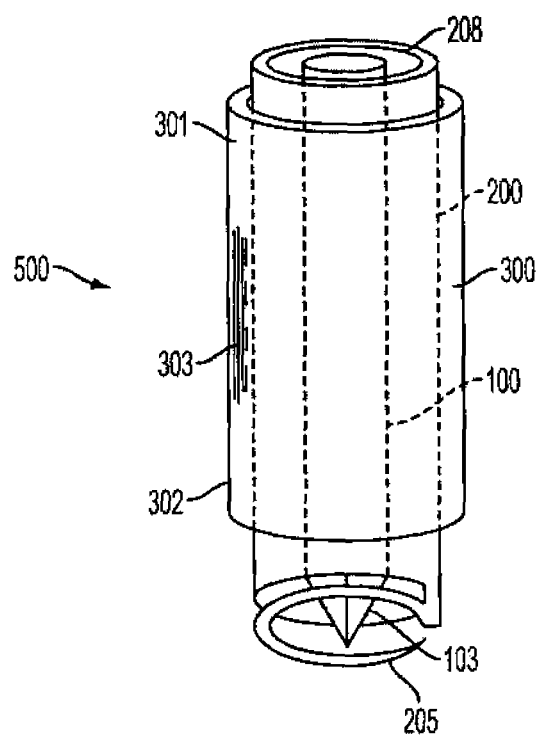
FIG. 17 depicts an embodiment incorporating a third elongated member substantially enclosing the embodiment of FIG. 3.

FIG. 17 depicts an embodiment of an apparatus 500 comprising a third elongated member 300 comprising a proximal end 301, a distal end 303, and a middle portion 302. In this embodiment, the third elongated member encloses the second elongated member 200 and the first elongated member 100. Regarding the third elongated member 300, it should be appreciated that the contours, shapes, lengths, and dimensions may be of any variety disclosed for the first and second elongated members, as well as desired or required. The third elongated member may be configured to accommodate a variety of devices or structures as desired or required. It should be appreciated that the third elongated member doesn't necessarily need to complete enclose the first and second elongated members.

Figure 18:
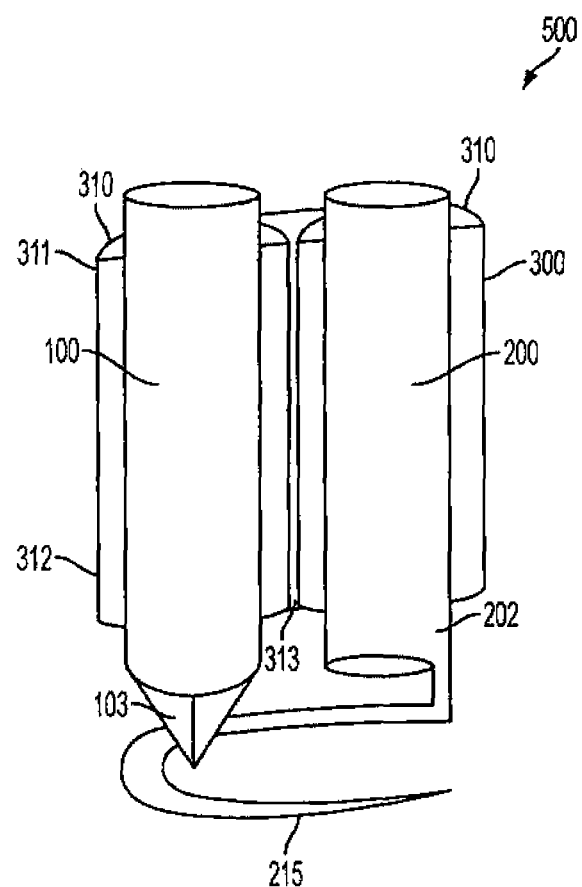
FIG. 18 depicts an alternate embodiment of the third elongated member with an alternate embodiment of the helical tine of the second elongated member.

FIG. 18 depicts an embodiment of the third elongated member 300. This embodiment comprises two substantially parallel tracks 310 for holding the first elongated member 100 and the second elongated member 200. The second elongated member has disposed at its distal end 202 the helical tine 215, wherein the helical tine has a cross-section such that the sharp end 103 of the first elongated member 100 is inside the cross section of the helical tine 215. Regarding the third elongated member 300, it should be appreciated that the contours, shapes, lengths, and dimensions may be of any variety disclosed for the first and second elongated members, as well as desired or required. The third elongated member may be configured to accommodate a variety of devices or structures as desired or required. The tracks 310 may be composed of silicone rubber, silicon, rubber, plastic, polymer, cloth, metal, foam, or any type of composite material or substance. In an approach, the two tracks 310 may be joined by a central body component 313. It should be appreciated that there may be less than two tracks or more that two tracks. Moreover, it should be appreciated that the first and second elongated members may be disposed inside one another as discussed in this disclosure, rather than side by side. Moreover, the side-by-side arrangement of the first and second elongated members may be implemented with the third elongated member as shown in FIG. 17, whereby the first and second elongated members are enclosed or at least substantially enclosed by the third elongated member.

Figure 19:
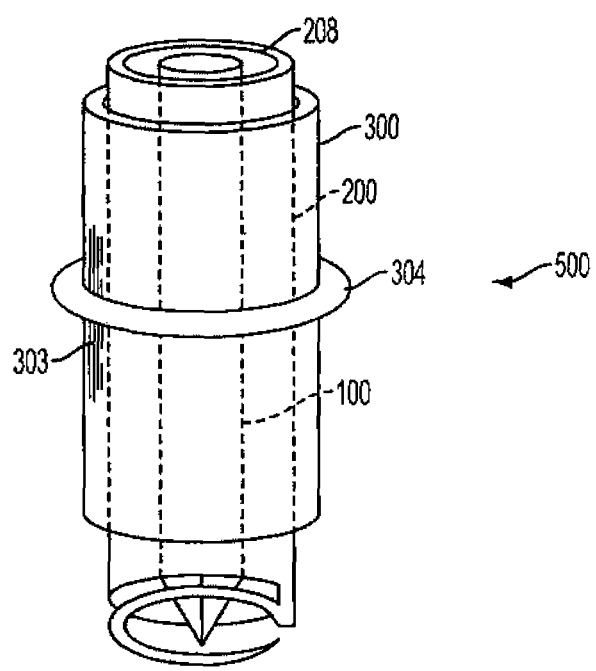
FIG. 19 depicts the embodiment in FIG. 17 with an optional skin bumper for stabilizing the device at the skin.

FIG. 19 depicts an embodiment of the apparatus 500 further comprising a skin bumper 304 attached to or in communication of the exterior of the middle portion 303 of the third elongated member 300. This skin bumper 304 is used for stabilizing the combination apparatus 500 on the skin of the subject. In an embodiment, the skin bumper 304 may be configured as a donut composed of silicone rubber, though other geometric configurations, contours, shapes, sizes and materials may be used. For example, the skin bumper may instead be composed of silicon, rubber, plastic, polymer, cloth, metal, foam, or any other type of composite material or substance.

Figure 20:
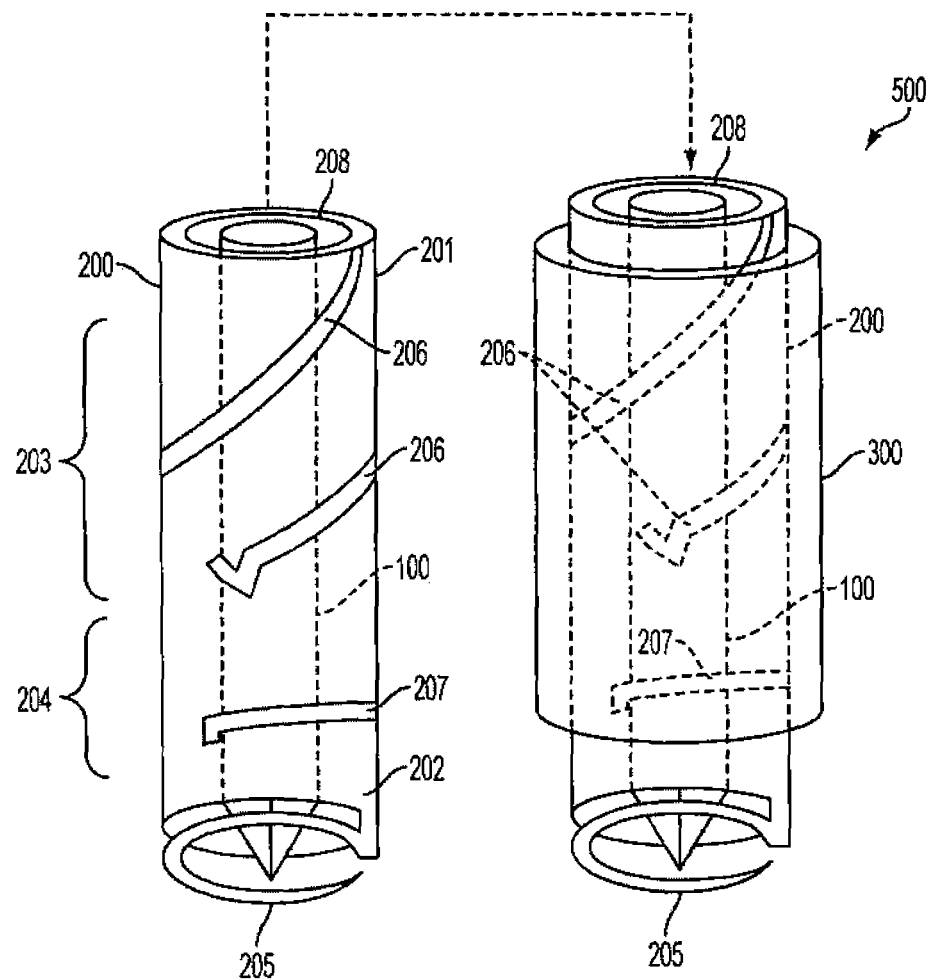
FIG. 20 depicts grooves in the second elongated member of the embodiment in FIG. 17.

FIG. 20 depicts an embodiment of the second elongated member 200 as a part of the apparatus 500. In this embodiment, the second elongated member 200 further comprises a first middle portion 204 adjacent to the distal end 202, and a second middle portion 203 adjacent to the proximal end 201. The second middle portion 203 further comprises a helical groove 206 bored into the surface (or provided in some appropriate technique) of the second elongated member 200 that terminates in a V-shape as shown (or in a shape as desired or required). The first middle portion 204 further comprises an L-shaped groove 207 bored into the surface of the second elongated member 200. The first elongated member 100 and second elongated member 200 are then placed inside the third elongated member 300.

Figure 21:
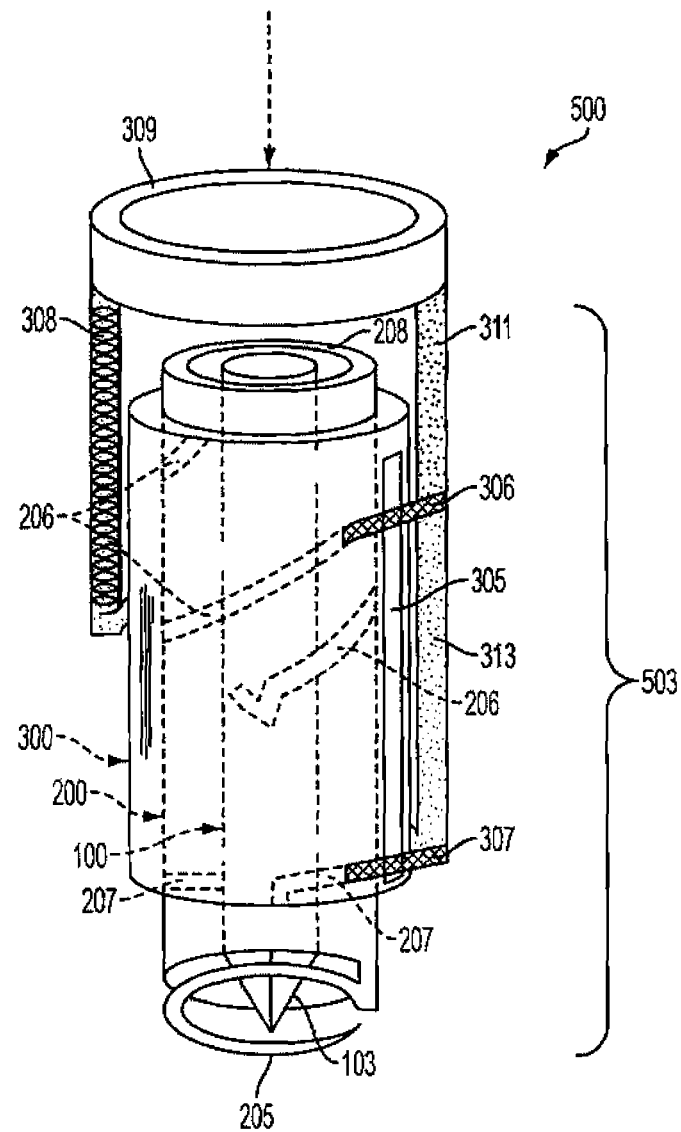
FIG. 21 depicts the actuator system for use with the embodiment in FIG. 20.

FIG. 21 depicts an embodiment of the apparatus 500 further comprising an actuator in a partially actuated state. In this embodiment, pressing down on the actuator button 309 causes an attached driver tab 306 passing through a longitudinal aperture 305 in the third elongated member 300 and engaged with the helical groove 206 to move in a distal direction, causing the interior first elongated member 100 and second elongated member 200 to advance in a distal direction while simultaneously causing the rotation of the second elongated member 200 and attached helical tine 205 as well as the compression of a spring 308. When the actuator button 309 is fully depressed, the driver tab 306 moves into the V-shaped terminus of the helical groove 206, holding the interior (i.e., first elongated member 100 and second elongated member 200) in a fixed position. When the actuator button 309 is depressed again from this position, the driver tab 306 is withdrawn from the V-shaped terminus, and the spring 308 drives the driver tab 306 back up the helical groove 206, causing the interior combination (i.e., first elongated member 100 and second elongated member 200 to rotate in the opposite direction and driving it in a proximal direction. In an embodiment the actuator button 309 is connected to a rigid actuator spine 311 to the driver tab 306. In an embodiment, the apparatus 500 also includes a restrictor tab 307 connected to the driver tab 306 by a compressible actuator spine 313. The restrictor tab 307 is adapted to pass through the longitudinal aperture 305 and to engage the L-shaped groove 207. This groove functions to stabilize the apparatus as it is actuated. It should be appreciated that a number of actuator devices or systems may be utilized that are configured to longitudinally drive the helical tine in a proximal and/or distal direction.

Figure 22:
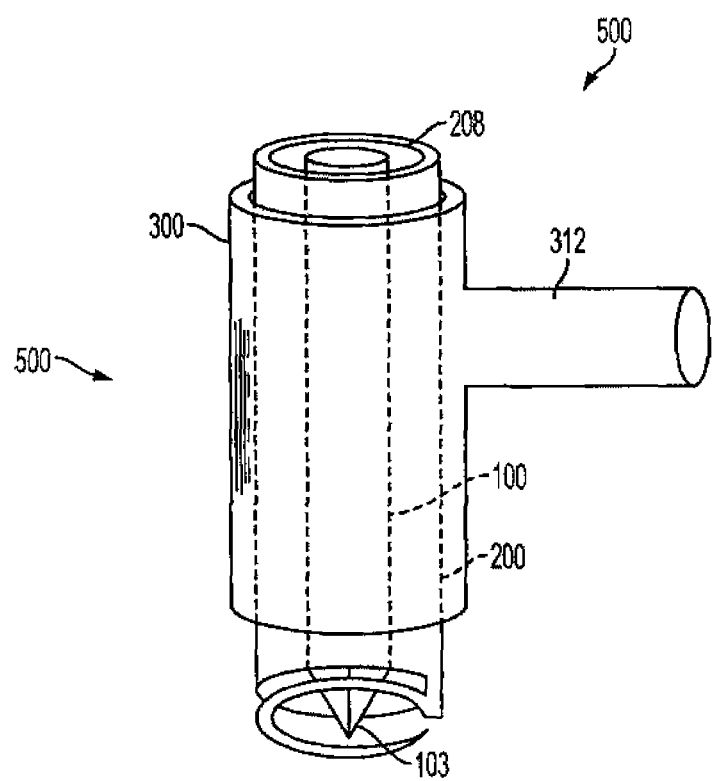
FIG. 22 depicts the embodiment in FIG. 17 with an optional side port.

FIG. 22 depicts an embodiment of the apparatus 500 wherein the third elongated member 300 further comprises a side port 312. The side port 312 may be used to infuse fluids into the anatomical space or to drain fluids from the anatomical space. The port may be utilized for egress and ingress. The port may be configured as more than one valve, two-way valve, channel, lumen or conduit, or the like.

Figure 23:
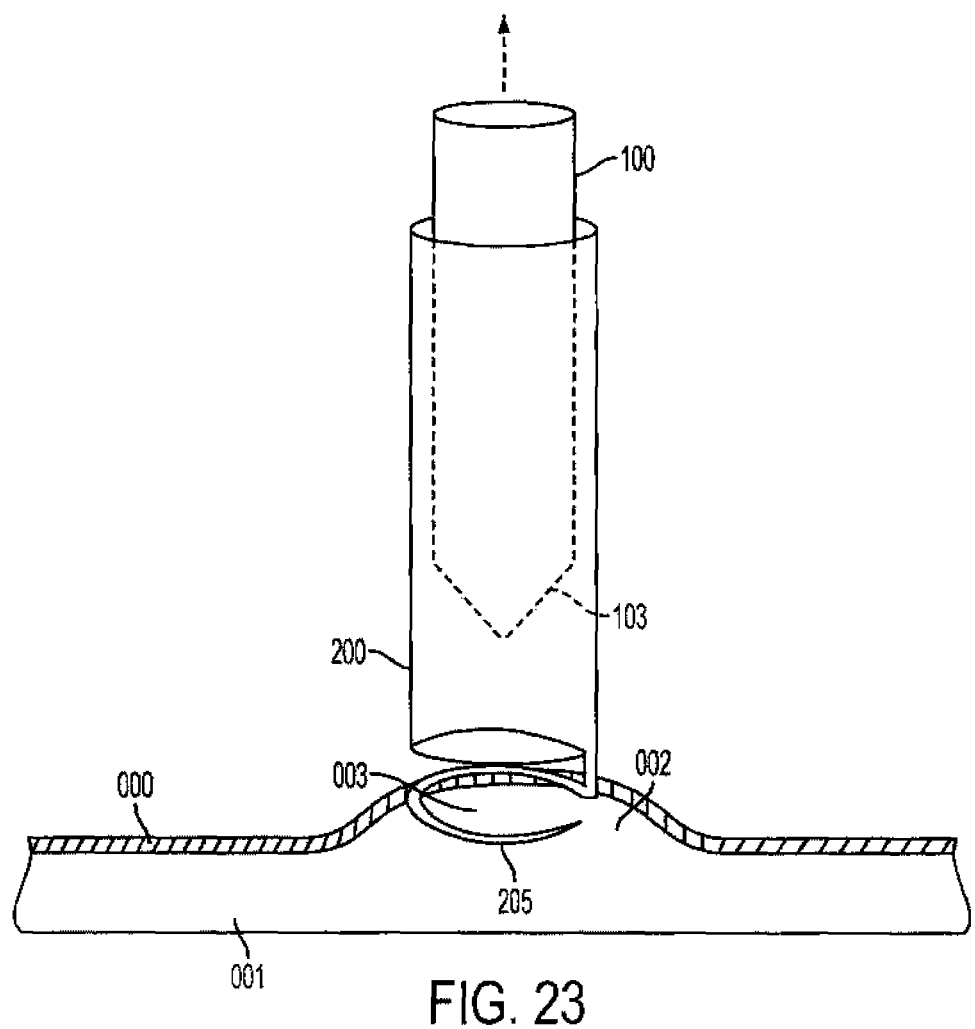
FIG. 23 depicts the withdrawal of the first elongated member once the anatomical space has been accessed using the embodiment in FIG. 3.
Figure 24:
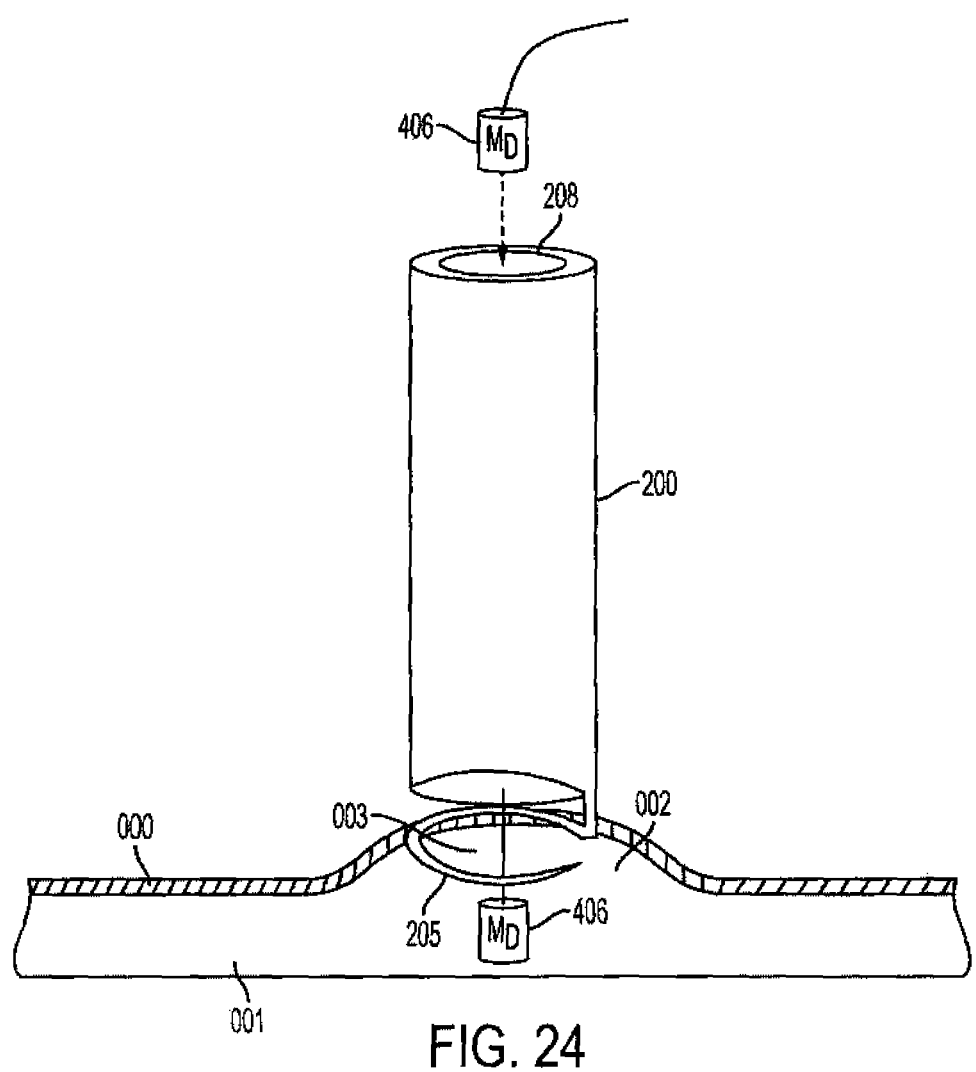
FIG. 24 depicts the embodiment of FIG. 23 wherein the second elongated member remains in place for use in introducing medical devices into the anatomical space.

FIGS. 23-26 depict various embodiments of different technique methods of the present invention. For instance, FIG. 23 illustrates that the first elongated member 100 is partially withdrawn from the system in a proximal direction, after the second elongated member 200 has been turned, the helical tine 205 has engaged and penetrated the surface 000, which as a result caused an expansion 002 of the anatomical space 001, and an incision 003 in the surface 000 by the sharp end. In an approach, the first elongated member 100 may be completely removed (but not necessarily) from the lumen 208 and a medical device 406 may be introduced through the lumen 208 before passing through the incision 003 and into the anatomical space 001, as shown in FIG. 24.

Although not shown, a medical device may be introduced into the incision while bypassing the first elongated member and/or second elongated member (and/or third elongated member). Moreover, the first elongated member may remain, may be removed or partially removed.

Figure 25:
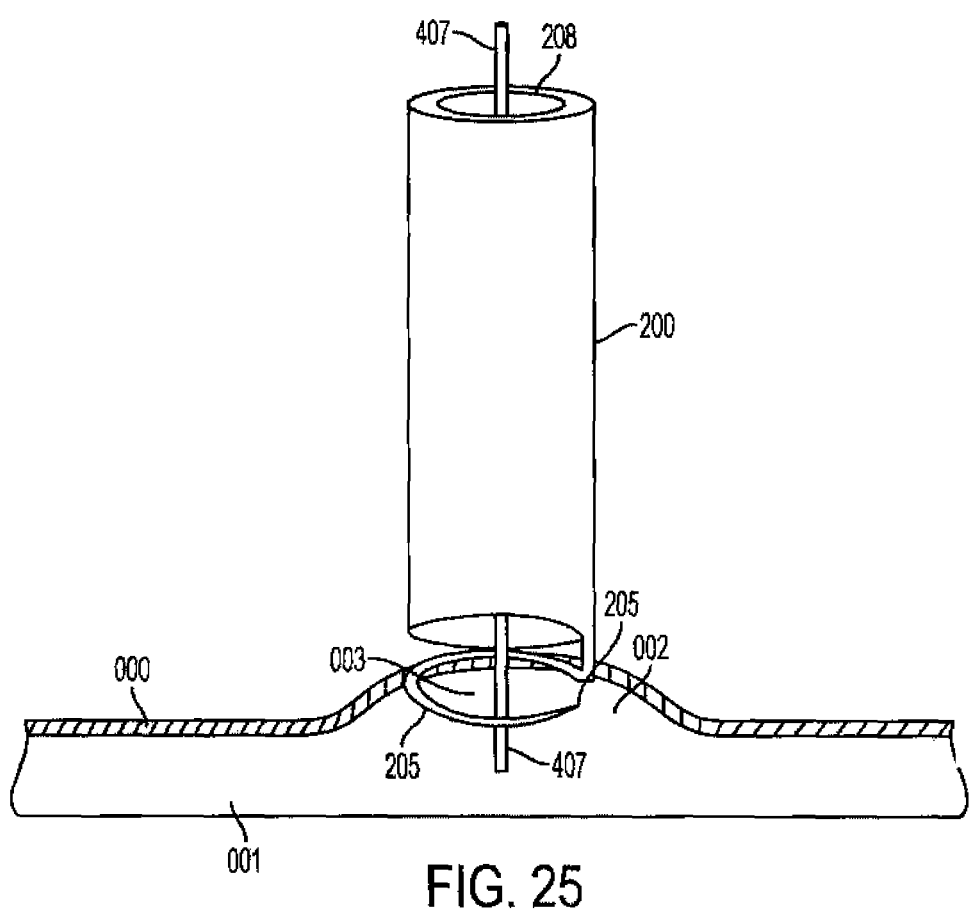
FIG. 25 depicts the embodiment of FIG. 24 wherein a guide wire is introduced into the anatomical space.
Figure 26:
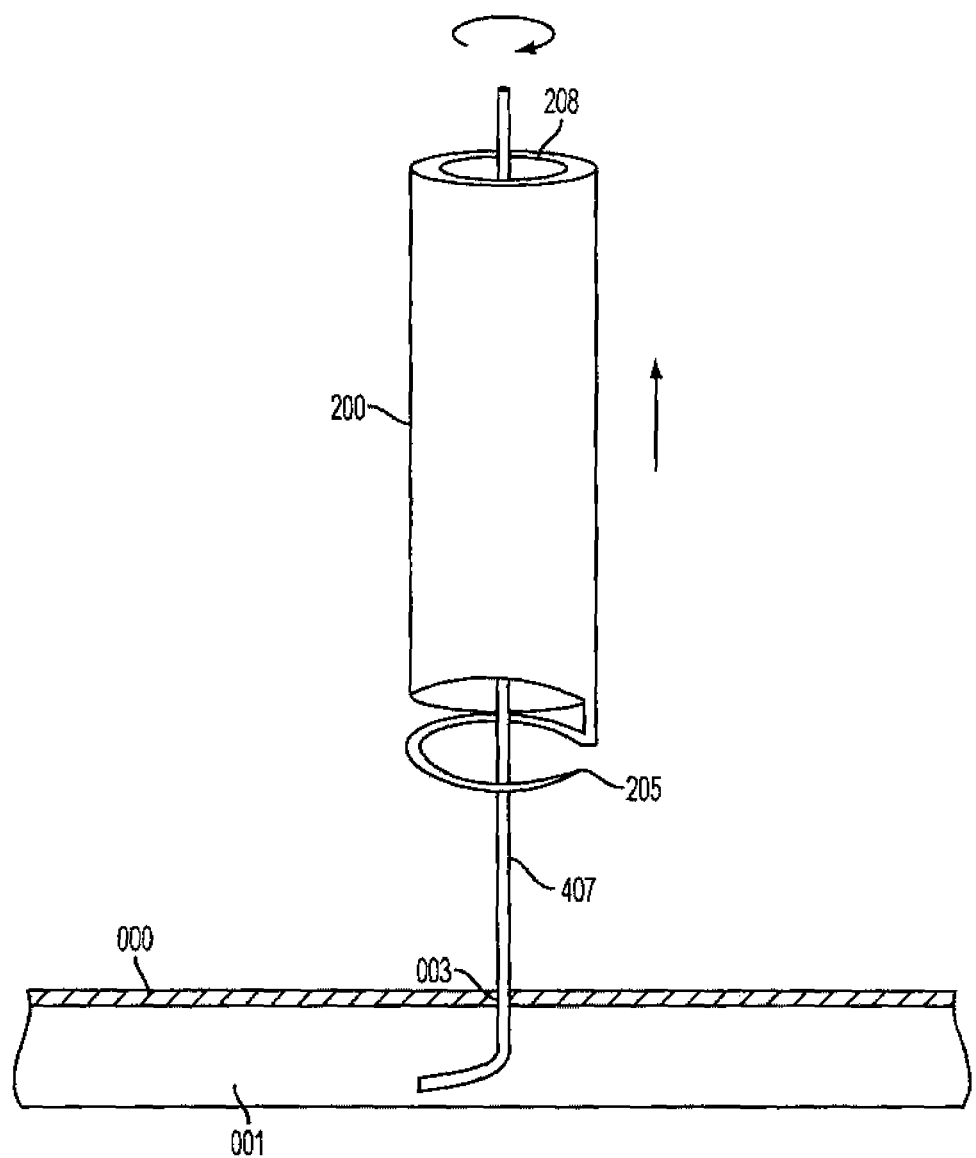
FIG. 26 depicts the embodiment of FIG. 25 wherein second elongated member is disengaged from the surface and withdrawn after the guide wire has been introduced into the anatomical space.

FIG. 25 illustrates an embodiment whereby a guide wire 407 is introduced through the lumen 208 before passing through the incision 003 and into the anatomical space 001. As shown in FIG. 26, once the guide wire 407 is inside the anatomical space 001, the second elongated member 200 may be rotated in the opposite direction of the initial rotation so that the helical tine 205 is disengaged from the surface 000. The second elongated member 200 is then withdrawn in a proximal direction.

Persons of ordinary skill in the art will understand and appreciate that a wide range of changes and modifications could be made to the embodiments described in detail above. As such, it is to be understood that the following claims, including all equivalents, are intended to define the scope of this invention.

It should be appreciated that any of the first, second and/or third elongated members may have one or more lumens there through. Such lumens may have a variety of cross-sections, diameter length, radius length, shape and contours. Moreover, the lumens may be multi-lumen or multi-channel.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

It should be appreciated that various sizes, dimensions, contours, rigidity, shapes, flexibility and materials of any of the embodiments discussed throughout may be varied and utilized as desired or required.

It should be appreciated that elongated members (first, second, and third) and their related components discussed herein may can take on all shapes along the entire continual geometric spectrum of manipulation of x, y and z planes to provide and meet the anatomical and structural demands and requirements. Size and shape of the elongated members (first, second, and third) during or prior to operation could also be manipulated by varying their compliance.

The devices, systems, compositions, computer program products, and methods of various embodiments of the invention disclosed herein may utilize aspects disclosed in the following references, applications, publications and patents and which are hereby incorporated by reference herein in their entirety:

U.S. patent application Ser. No. 12/760,837 entitled "Coaxial Catheter Systems for Transference of Medium," filed Apr. 15, 2010. (00877-04).

U.S. patent application Ser. No. 11/191,676 entitled "Coaxial Catheter Systems for Transference of Medium," filed Jul. 28, 2005. (00877-03), 2006-0025752 Feb. 2, 2006.

International Patent Application No. PCT/US2005/026738 entitled "Coaxial Catheter Systems for Transference of Medium," filed Jul. 28, 2005. (00877-02), WO06/15091 Feb. 9, 2006.

U.S. patent application Ser. No. 12/625,153 entitled "Blood Flow Bypass Catheters and Methods for the Delivery of Medium to the Vasculature and Body Ducts," filed Nov. 24, 2009. (01098-04).

U.S. patent application Ser. No. 11/884,421 entitled "Blood Flow Bypass Catheters and Methods for the Delivery of Medium to the Vasculature and Body Ducts," filed Aug. 15, 2007. (01098-03), US2008/0262467 A1 Oct. 23, 2008.

International Patent Application No. US2006/005876 entitled "Blood Flow Bypass Catheters and Methods for the Delivery of Medium to the Vasculature and Body Ducts," filed Feb. 16, 2006. (01098-02), WO06089243 Aug. 24, 2006.

U.S. patent application Ser. No. 12/532,233 entitled "Electrode Catheter for Ablation Purposes and Related Method Thereof," filed Sep. 21, 2009. (01380-03).

International Patent Application No. PCT/US2008/057626 entitled "Electrode Catheter for Ablation Purposes and Related Method Thereof," filed Mar. 20, 2008. (01380-02), WO 2008/118737 Oct. 2, 2008.

U.S. patent application Ser. No. 12/530,938 entitled "Epicardial Ablation Catheter and Method of Use," filed Sep. 11, 2009. (01363-03).

International Patent Application No. PCT/US2008/056816 entitled "Epicardial Ablation Catheter and Method of Use," filed Mar. 13, 2008. (01363-02), WO 2008/112870 Sep. 18, 2008.

U.S. patent application Ser. No. 12/530,830 entitled "Access Needle Pressure Sensor Device and Method of Use," filed Sep. 11, 2009. (01378-03), 2010/0094143 Apr. 15, 2010.

International Patent Application No. PCT/US2008/056643 entitled "Access Needle Pressure Sensor Device and Method of Use," filed Mar. 12, 2008. (01378-02), WO 2008/115745 Sep. 25, 2008.

International patent application Ser. No. 12/304,801 entitled "Closure Device for Skull Plates and Related Method Thereof," filed May 18, 2009. (01270-03), 2010/0042158 Feb. 18, 2010.

International Patent Application No. PCT/US2007/014881 entitled "Closure Device for Skull Plates and Related Method Thereof," filed Jun. 26, 2007. (01270-02), WO20082595 Jan. 3, 2008.

U.S. patent application Ser. No. 12/513,258 entitled "Means and Methods for Cytometric Therapies," filed May 1, 2009. (01321-06).

International Patent Application No. PCT/US2007/023047 entitled "Means and Methods for Cytometric Therapies," filed Nov. 1, 2007. (01321-02), WO 2008/057370 May 15, 2008.

U.S. patent application Ser. No. 12/375,139 entitled "System and Method for Intracranial Implantation of Therapeutic or Diagnostic Agents," filed Jan. 27, 2009. (01277-03), 2009-0192487 Jul. 30, 2009.

International Patent Application No. PCT/US2007/016256 entitled "System and Method for Intracranial Implantation of Therapeutic or Diagnostic Agents," filed Jul. 18, 2007. (01277-02), WO2008/013709 Jan. 31, 2008.

International Patent Application No. PCT/US2008/082835 entitled "STEERABLE EPICARDIAL PACING CATHETER SYSTEM PLACED VIA THE SUBXIPHOID PROCESS," filed Nov. 7, 2008. (01473-02), WO 2009/062061 May 14, 2009.

U.S. patent application Ser. No. 12/160,378 entitled "Multi-Port Catheter System with Medium Control and Measurement Systems for Therapy and Diagnosis Delivery," filed Aug. 1, 2008. (01080-04), 2009-0048577 Feb. 19, 2009.

International Patent Application No. PCT/US2007/000353 entitled "Multi-Port Catheter System with Medium Control and Measurement Systems for Therapy and Diagnosis Delivery," filed Jan. 9, 2007. (01080-03), WO/2007/081842 Jul. 19, 2007.

International Patent Application No. US2006/013621 entitled "Catheter Systems for Delivery of Agents and Related Method Thereof," filed Apr. 12, 2006. (00982-03) WO06113267 Oct. 26, 2006.

U.S. patent application Ser. No. 11/105,166 entitled "Catheter Systems for Delivery of Agents and Related Method Thereof," filed Apr. 13, 2005. (00982-02), 2005/0245896 Nov. 3, 2005, U.S. Pat. No. 7,670,327 Mar. 2, 2010.

U.S. patent application Ser. No. 10/985,340 entitled "Catheter Navigation Within an MR Imaging Device," filed Nov. 10, 2004. (00681-04) 0119556 Jun. 2, 2005.

U.S. patent application Ser. No. 10/429,524 entitled "Catheter Navigation Within an MR Imaging Device," filed May 5, 2003. (00681-03), 030195412 Oct. 16, 2003, U.S. Pat. No. 6,834,201 Dec. 21, 2004.

International patent application Ser. No. 02/02363 entitled "Catheter Navigation within an MR Imaging Device," filed Jan. 28, 2002. (00681-02).

U.S. patent application Ser. No. 09/772,188 entitled "Catheter Navigation within an MR Imaging Device," filed Jan. 29, 2001. (00681-01).

U.S. patent application Ser. No. 10/444,884 entitled "Cell Delivery Catheter and Method," filed May 23, 2003. (00827-03), 2003/0204171 Oct. 30, 2003.

U.S. patent application Ser. No. 09/574,857 entitled "Cell Delivery Catheter and Method," filed May 19, 2000. (00827-02), U.S. Pat. No. 6,599,274 Jul. 29, 2003.

U.S. patent application Ser. No. 09/548,110 entitled "Multi-Probe System," filed Apr. 12, 2000. (00578-01, U.S. Pat. No. 6,626,902 Sep. 30, 2003.

International Patent Application No. US99/24253 entitled "MRI AND MAGNETIC STEREOTAXIS SURGICAL SYSTEM," filed Oct. 15, 1999. (00198-02), WO00/23000 Apr. 27, 2000.

U.S. patent application Ser. No. 09/174,189 entitled "Combined Magnetic Resonance Imaging and Magnetic Stereotaxis Surgical Apparatus and Processes," filed Oct. 16, 1998. (00198-01), U.S. Pat. No. 6,298,259 Oct. 2, 2001.

U.S. patent application Ser. No. 99/17880 entitled "MR-Visible Device for Magnetic Stereotaxis Neurological Interventions," filed Aug. 6, 1999. (00199-02), WO00/07652 Feb. 17, 2000.

U.S. patent application Ser. No. 09/131,031 entitled "MR-Visible Medical Device for Neurological Interventions Using Nonlinear Magnetic Stereotaxis and a Method Imaging," filed Aug. 7, 1998. (00199-01), U.S. Pat. No. 6,272,370 Aug. 7, 2001.

U.S. patent application Ser. No. 09/114,414 entitled "Magnetic Stereotactic System for Treatment Delivery," filed Jul. 13, 1998. (00220-05), U.S. Pat. No. 6,216,030 Apr. 10, 2001.

U.S. patent application Ser. No. 08/464,279 entitled "Magnetic Stereotactic System for Treatment Delivery," filed Jun. 5, 1995. (00220-04), U.S. Pat. No. 5,707,335 Jan. 13, 1998.

U.S. patent application Ser. No. 08/096,214 entitled "Magnetic Stereotactic System for Treatment Delivery," filed Jul. 19, 1993. (00220-03), U.S. Pat. No. 5,779,694 Jul. 14, 1998.

U.S. patent application Ser. No. 07/904,032 entitled "MAGNETIC STEREOTACTIC SYSTEM FOR TREATMENT DELIVERY," filed Jun. 25, 1992. (00220-02).

U.S. patent application Ser. No. 07/463,340 entitled "Magnetic Stereotactic System for Treatment Delivery," filed Jan. 10, 1990. (00220-01), U.S. Pat. No. 5,125,888 Jun. 30, 1992.

1. U.S. Pat. No. 6,423,051 B1 to Kaplan, et al., Jul. 23, 2002, "Methods and Apparatus for Pericardial Access".

2. U.S. Pat. No. 6,156,009 to Grabek, J., Dec. 5, 2000, "Apparatus for Accessing the Pericardial Space".

3. U.S. Pat. No. 6,592,552 B1 to Schmidt, C., Jul. 15, 2003, "Direct Pericardial Access Device and Method".

4. U.S. Pat. No. 6,162,195 to Igo, et al., Dec. 19, 2000, "Method and Apparatus for Accessing the Pericardial Space".

5. U.S. Patent Application Publication No. US2008/0108945 A1 to Kaplan, et al., May 8, 2008, "Methods and Apparatus for Pericardial Access".

6. U.S. Pat. No. 7,309,328 B2 to Kaplan et al., Dec. 18, 2007, "Methods and Apparatus for Pericardial Access."

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. An apparatus for accessing a subject's anatomical space having a surface, the apparatus comprising:

a first elongated member comprising a proximal end and a distal end, said distal end comprising a sharp end;

a second elongated member comprising a proximal end, a distal end, a first middle portion adjacent to said distal end, and a second middle portion adjacent to said proximal end, said second middle portion of said second elongated member including a helical groove, and said distal end comprising a helical tine;

a third elongated member comprising a longitudinal aperture, a distal end, a middle portion, and a proximal end, wherein said third elongated member at least substantially encloses said first elongated member and said second elongated member; and a driving mechanism including:
  a driver tab, said driver tab adapted to pass through said longitudinal aperture of said third elongated member and engage said helical groove of said second elongated member, wherein:
    if said driver tab is moved distally then said tab drives said second elongated member in a distal direction;
    if said driver tab is moved proximally then said tab drives said second elongated member in a proximal direction,
  wherein said helical tine is adapted to:
    engage and penetrate said surface, and wherein when said second elongated member is turned, said helical tine lifts said surface in a proximal direction.

2. The apparatus of claim 1, wherein said first elongated member comprises at least one lumen.

3. The apparatus of claim 2, wherein said second elongated member is inside said at least one lumen of said first elongated member.

4. The apparatus of claim 3, wherein sharp end of said first elongated member is configured as a sharp rim.

5. The apparatus of claim 3, wherein said second elongated member comprises at least one lumen.

6. The apparatus of claim 2, wherein said second elongated member is outside said at least one lumen of said first elongated member.

7. The apparatus of claim 6, wherein said second elongated member is at least one lumen, wherein said at least one lumen of side second elongated member is outside said lumen of said lumen of said first elongated member.

8. The apparatus of claim 6, wherein said sharp end of said first elongated member is configured as a point.

9. The apparatus of claim 6, wherein said end comprises at least one of the following; beveled structure, serrated structure, tapered structure, or cutting edge structure.

10. The apparatus of claim 1, wherein said second elongated member is outside said first elongated member.

11. The apparatus of claim 10, wherein said second elongated member comprises at least one lumen, wherein said at least one lumen of said second elongated member is outside said first elongated member.

12. The apparatus of claim 10, wherein sharp end of said first elongated member is configured as a point.

13. The apparatus of claim 10, wherein said end comprises at least one of the following; beveled structure, serrated structure, tapered structure, or cutting edge structure.

14. The apparatus of claim 1, wherein said second elongated member comprises at least one lumen.

15. The apparatus of claim 1, wherein said advancing of said surface in contact with said sharp end is caused by either:
  a) said lift of the surface;
  b) said lift of the surface and a movement of said first elongated member in distal direction;
  c) said lift of the surface and a movement of said second elongated member in a proximal direction; or
  d) said lift of the surface, a movement of said first elongated member in a distal direction and a movement of said second elongated member in a proximal direction.

16. The apparatus of claim 1, wherein said helical tine is defined by a lateral cross-section, wherein said lateral cross-section of said helical tine has an area that defines the geometry of the surface being lifted to provide a surface contact.

17. The apparatus of claim 1, wherein said anatomical space comprises a pericardial space.

18. The apparatus of claim 17, wherein said surface is the parietal pericardium.

19. The apparatus of claim 1, wherein said anatomical space comprises a kidney, a brain, a blood vessel, a peritoneal cavity, a spinal cord, an intra-abdominal space, an intrathoracic space or any space in the body bounded by a membrane or membranous entity.

20. The apparatus of claim 19, wherein said surface is a renal capsule, a dura mater, a blood vessel wall, a peritoneum, a dural lining of the spinal cord, a pleura, a seurosa, or any other membrane in the body.

21. The apparatus of claim 1, further comprising an access needle, said access needle adapted to be navigated and inserted into the anatomical space.

22. The apparatus of claim 21, wherein said first elongated member and said second elongated member are configured to be used in conjunction with said access needle.

23. The apparatus of claim 22, wherein said conjunction is an insertion through said access needle.

24. The apparatus of claim 1, further comprising a pressure sensing means configured to identify the different pressure-frequency regimes of the tissues through which said elongated members are being moved.

25. The apparatus of claim 1, wherein said apparatus is adapted to be visible on a medical imaging modality.

26. The apparatus of claim 25, wherein said medical imaging modality comprises at least one of magnetic resonance imaging, computed tomography, fluoroscopy, ultrasound, or other radiological modalities.

27. The apparatus of claim 25, wherein said medical imaging modality further comprises display means for displaying said sharp end's position or communication means for communicating said sharp end's position.

28. The apparatus of claim 1, further comprising switchable means for holding said first elongated member in a fixed position with respect to said second elongated member.

29. The apparatus of claim 1,
  wherein said third elongated member is further configured to retain said first elongated member and said second elongated member to a movement that is at least substantially longitudinal as defined by the proximal and distal directions.

30. The apparatus of claim 1, wherein said third elongated member further comprises a side port.

31. The apparatus of claim 30, wherein said side port is adjacent to said proximal end of said third elongated member.

32. The apparatus of claim 1, further comprising means for stabilizing said third elongated member on a subject's skin.

33. The apparatus of claim 1, further comprising a bumper disposed to said middle portion of said third elongated member.

34. The apparatus of claim 33, wherein said bumper comprises at least one of the following: silicone rubber, silicon, rubber, plastic, polymer, cloth, metal, foam, or any type of composite material or substance.

35. The apparatus of claim 1, wherein said first middle portion further comprises an L-shaped groove.

36. The apparatus of claim 35, further comprising a restricting tab adapted to pass through said longitudinal aperture and engage said L-shaped groove, thereby restricting said second elongated member regarding its distal longitudinal movement.

37. The apparatus of claim 1, further comprising actuator means for longitudinally driving said helical tine in a proximal and/or distal direction.

* * * * *